(12) United States Patent
Zocchi

(10) Patent No.: US 8,257,258 B2
(45) Date of Patent: Sep. 4, 2012

(54) INTEGRATED LANCET AND BLOOD GLUCOSE METER SYSTEM

(75) Inventor: Michael R. Zocchi, Somerville, MA (US)

(73) Assignee: Abbott Laboratories, Abbott Park, IL (US)

( * ) Notice: Subject to any disclaimer, the term of this patent is extended or adjusted under 35 U.S.C. 154(b) by 1320 days.

(21) Appl. No.: 11/830,760

(22) Filed: Jul. 30, 2007

(65) Prior Publication Data

US 2008/0021291 A1  Jan. 24, 2008

Related U.S. Application Data

(63) Continuation of application No. 10/899,773, filed on Jul. 27, 2004, now Pat. No. 7,512,432.

(51) Int. Cl.
*A61B 5/05* (2006.01)
(52) U.S. Cl. .......... 600/365; 600/345; 600/347
(58) Field of Classification Search ........... 600/345, 600/347, 365; 204/403.01–403.15, 416–418; 205/777.5, 778; 436/44, 47–49; 606/183; 422/50

See application file for complete search history.

(56) References Cited

U.S. PATENT DOCUMENTS

| | | | |
|---|---|---|---|
| 4,218,421 A | 8/1980 | Mack, Jr. et al. | |
| 4,328,184 A | 5/1982 | Kondo | |
| 4,580,564 A | 4/1986 | Andersen | |
| 4,817,119 A | 3/1989 | Ledley et al. | |
| 4,895,147 A | 1/1990 | Bodicky et al. | |
| 4,909,260 A | 3/1990 | Salem et al. | |
| 5,074,977 A | 12/1991 | Cheung et al. | |
| 5,108,889 A | 4/1992 | Smith et al. | |
| 5,152,775 A | 10/1992 | Ruppert | |
| 5,231,993 A | 8/1993 | Haber et al. | |
| 5,279,294 A | 1/1994 | Anderson et al. | |
| 5,395,504 A | 3/1995 | Saurer et al. | |

(Continued)

FOREIGN PATENT DOCUMENTS

DE  19819407  11/1999

(Continued)

OTHER PUBLICATIONS

Abstract of Japanese Publication No. JP-08-320304 Published Mar. 12, 1996.

(Continued)

*Primary Examiner* — Michael Kahelin
*Assistant Examiner* — Christian Jang
(74) *Attorney, Agent, or Firm* — Jackson & Co., LLP

(57) ABSTRACT

A sensor array designed to be continuously indexed through a compatible blood glucose test monitor for the purpose of conducting multiple consecutive blood glucose measurements. The sensor array can be configured to substantially conform to a non-planar surface. In one embodiment, the sensor array includes first and second test sensors which are hingedly coupled together through a pin and socket interconnection. In another embodiment, the sensor array includes a unitary, non-conductive substrate which is scored to define one or more fold lines, a first set electrodes deposited on the substrate to define a first test sensor, and a second set of electrodes deposited on the substrate to define a second test sensor. In another embodiment, the sensor array includes a first test sensor, a second test sensor spaced apart from said first test sensor, a first spacer mounted on the first test sensor, a second spacer mounted on the second test sensor, and a unitary flexible member disposed across said first and second spacers.

6 Claims, 19 Drawing Sheets

U.S. PATENT DOCUMENTS

| | | |
|---|---|---|
| 5,487,748 A | 1/1996 | Mershell et al. |
| 5,538,493 A | 7/1996 | Gerken et al. |
| 5,575,403 A | 11/1996 | Charlton et al. |
| 5,609,823 A | 3/1997 | Hartig et al. |
| 5,621,613 A | 4/1997 | Haley et al. |
| 5,630,986 A | 5/1997 | Charlton et al. |
| 5,739,426 A | 4/1998 | Storm |
| 5,741,634 A | 4/1998 | Nozoe et al. |
| RE35,803 E | 5/1998 | Lanqe et al. |
| 5,802,940 A | 9/1998 | Jaeger |
| 5,872,713 A | 2/1999 | Douglas |
| 5,904,898 A | 5/1999 | Markart |
| 5,942,102 A | 8/1999 | Hodges et al. |
| 5,997,817 A | 12/1999 | Crismore et al. |
| 6,027,459 A | 2/2000 | Shain et al. |
| 6,056,701 A | 5/2000 | Duchon et al. |
| 6,063,039 A | 5/2000 | Cunningham et al. |
| 6,093,156 A | 7/2000 | Cunningham et al. |
| 6,143,164 A | 11/2000 | Heller et al. |
| 6,151,110 A | 11/2000 | Markart |
| 6,174,420 B1 | 1/2001 | Hodges et al. |
| 6,179,999 B1 | 1/2001 | Sherman et al. |
| 6,315,738 B1 | 11/2001 | Nishikawa et al. |
| 6,332,871 B1 | 12/2001 | Douglas et al. |
| 6,352,514 B1 | 3/2002 | Douglas et al. |
| 6,464,649 B1 | 10/2002 | Duchon et al. |
| 6,506,168 B1 | 1/2003 | Fathallah et al. |
| 6,544,475 B1 | 4/2003 | Douglas et al. |
| 6,561,989 B2 | 5/2003 | Whitson |
| 6,602,268 B2 | 8/2003 | Kuhr et al. |
| 6,616,616 B2 | 9/2003 | Fritz et al. |
| 6,706,049 B2 | 3/2004 | Moerman |
| 6,767,440 B1 | 7/2004 | Bhullar et al. |
| 6,783,502 B2 | 8/2004 | Orloff et al. |
| 6,849,052 B2 | 2/2005 | Uchiqaki et al. |
| 6,949,111 B2 | 9/2005 | Schraga |
| 7,211,096 B2 | 5/2007 | Kuhr et al |
| 7,238,192 B2 | 7/2007 | List et al. |
| 7,273,484 B2 | 9/2007 | Thoes et al. |
| 7,299,081 B2 | 11/2007 | Mace et al. |
| 7,303,726 B2 | 12/2007 | McAllister et al. |
| 7,316,700 B2 | 1/2008 | Alden et al. |
| 2002/0002344 A1 | 1/2002 | Douglas et al. |
| 2003/0085124 A1 | 5/2003 | Ufer |
| 2003/0191415 A1 | 10/2003 | Moerman et al. |
| 2003/0211619 A1* | 11/2003 | Olson et al. ................ 436/44 |
| 2004/0087033 A1 | 5/2004 | Schembri |
| 2004/0138588 A1 | 7/2004 | Saikley et al. |
| 2004/0225311 A1 | 11/2004 | Levauqhn et al. |
| 2005/0019212 A1 | 1/2005 | Bhullar et al. |
| 2005/0096519 A1 | 5/2005 | DeNuzzio et al. |
| 2005/0145020 A1 | 7/2005 | Mathur et al. |
| 2005/0239156 A1 | 10/2005 | Drucker et al. |
| 2005/0245844 A1 | 11/2005 | Mace et al. |
| 2005/0277164 A1 | 12/2005 | Drucker et al. |
| 2005/0277850 A1 | 12/2005 | Mace et al. |
| 2006/0024774 A1 | 2/2006 | Zocchi |
| 2006/0025662 A1 | 2/2006 | Buse et al. |
| 2006/0094985 A1 | 5/2006 | Aceti et al. |
| 2006/0191787 A1 | 8/2006 | Wang et al. |
| 2006/0266644 A1 | 11/2006 | Pugh et al. |
| 2007/0149897 A1 | 6/2007 | Ghesquiere et al. |
| 2008/0021291 A1 | 1/2008 | Zocchi |
| 2008/0021295 A1 | 1/2008 | Wang et al. |
| 2008/0021493 A1 | 1/2008 | Levauqhn et al. |
| 2008/0027302 A1 | 1/2008 | Buse et al. |
| 2008/0033318 A1 | 2/2008 | Mace et al. |
| 2008/0167578 A1 | 7/2008 | Bryer et al. |
| 2008/0188732 A1 | 8/2008 | Mace et al. |

FOREIGN PATENT DOCUMENTS

| | | |
|---|---|---|
| EP | 1360935 | 11/2003 |
| JP | 8-320304 | 3/1996 |
| WO | WO-2005/107594 | 11/2005 |
| WO | WO-2006/019665 | 2/2006 |
| WO | WO-2008/039946 | 4/2008 |
| WO | WO-2008/039949 | 4/2008 |

OTHER PUBLICATIONS

PCT Application No. PCT/US2005/024455, International Search Report and Written Opinion of the International Searching Authority mailed Oct. 27, 2005.

PCT Application No. PCT/US2005/024455, International Preliminary Report on Patentability and Written Opinion of the International Searching Authority mailed Jan. 30, 2007.

U.S. Appl. No. 10/899,773, Notice of Allowance mailed Dec. 2, 2008.

U.S. Appl. No. 10/899,773, Office Action mailed Aug. 7, 2008.

U.S. Appl. No. 10/899,773, Office Action mailed Nov. 26, 2007.

U.S. Appl. No. 10/899,773, Office Action mailed Feb. 8, 2007.

* cited by examiner

INTEGRATED LANCET AND BLOOD GLUCOSE METER SYSTEM

PRIORITY

This application is a continuation of U.S. patent application Ser. No. 10/899,773, filed Jul. 27, 2004, and is hereby incorporated by reference.

BACKGROUND OF THE INVENTION

The present invention relates generally to analyte test sensors and more particularly to a novel array of analyte test sensors.

There are many medical conditions which require frequent measurement of the concentration of a particular analyte in the blood of a patient. For example, diabetes is a disease which typically requires a patient to routinely measure the concentration of glucose in his/her blood. Based upon the results of each blood glucose measurement, the patient may then require a particular drug treatment (e.g., an injection of insulin) in order to regulate that the blood glucose level of the patient remains within a specified range. Exceeding the upper limit of said range (hyperglycemia) or dropping beneath the lower limit of said range (hypoglycemia) should be avoided with as much diligence as possible to prevent the patient from experiencing serious medical complications which include, inter alia, retinopathy, nephropathy, and neuropathy.

A multi-step process is commonly practiced by diabetes patients to self-monitor the level of glucose present in their blood.

In the first step of said process, a patient is required to provide a blood sample suitable for testing. Blood samples taken from a patient for blood sugar monitoring are typically obtained by piercing the skin of the patient using a lancet device. A lancet device typically includes a body and a lancet. The body is typically adapted to be held by the user, the lancet being coupled to the body and being adapted to penetrate through the epidermis (the outermost layer of the skin) of the patient and into the dermis (the layer of skin directly beneath the epidermis) which is replete with capillary beds. The puncture of one or more capillaries by the lancet generates a sample of blood which exits through the incision in the patient's skin.

In some lancet devices, the lancet extends from the body at all times. In other lancet devices, the lancet is adapted to be moved, when actuated, from a retracted position in which the lancet tip is disposed within the body to an extended position in which the lancet tip extends beyond the body. Typically, the movement of the lancet from its retracted position to its extended position is effected with such force that contact of the moving lancet tip with the skin of a patient results in the piercing of the skin of the patient. In many such lancet devices having a movable lancet, the lancet is automatically drawn back into the body after reaching its extended position (e.g., using a spring) in order to minimize the risk of inadvertent lancet sticks.

In the second step of said process, a blood glucose monitoring system is utilized to measure the concentration of glucose in the blood sample. One type of glucose monitoring system which is well known and widely used in the art includes a blood glucose meter (also commonly referred to a blood glucose monitor) and a plurality of individual, disposable, electrochemical test sensors which can be removably loaded into the meter. Examples of blood glucose monitoring systems of this type are manufactured and sold by Abbott Laboratories, Medisense Products of Bedford, Mass. under the PRECISION line of blood glucose monitoring systems.

Each individual electrochemical test sensor typically includes a substrate which is formed as a thin, rectangular strip of non-conductive material, such as plastic. A plurality of carbon-layer electrodes are deposited (e.g., screen printed) on the substrate along a portion of its length in a spaced apart relationship, one electrode serving as the reference electrode for the test sensor and another electrode serving as the working electrode for the test sensor. All of the conductive electrodes terminate at one end to form a reaction area for the test sensor. In the reaction area, an enzyme is deposited on the working electrode. When exposed to the enzyme, glucose present in a blood sample undergoes a chemical reaction which produces a measurable electrical response. The other ends of the electrical contacts are disposed to electrically contact associated conductors located in the blood glucose monitor, as will be described further below.

A blood glucose monitor is typically modular and portable in construction to facilitate its frequent handling by the patient. A blood glucose monitor often comprises a multi-function test port which is adapted to receive the test sensor in such a manner so that an electrical communication path is established therebetween. As such, an electrical reaction created by depositing a blood sample onto the reaction area of the test sensor travels along the working electrode of the test sensor and into the test port of the blood glucose monitor. Within the housing of the monitor, the test port is electrically connected to a microprocessor which controls the basic operations of the monitor. The microprocessor, in turn, is electrically connected to a memory device which is capable of storing a multiplicity of blood glucose test results.

In use, the blood glucose monitoring system of the type described above can be used in the following manner to measure the glucose level of a blood sample and, in turn, store the result of said measurement into memory as test data. Specifically, a disposable test sensor is unwrapped from its packaging and is inserted into the test port of the monitor. With the test sensor properly inserted into the monitor, there is established a direct electrical contact between the conductors on the test sensor and the conductors contained within the test port, thereby establishing an electrical communication path between the test sensor and the monitor. Having properly disposed the test sensor into the test port, the monitor typically displays a "ready" indication on its display.

The user is then required to provide a blood sample using a lancet device. Specifically, a disposable lancet is unwrapped from its protective packaging and is loaded into a corresponding lancet device. The lancet device is then fired into the skin of the patient to provide a blood sample.

After lancing the skin, the patient is required to deposit one or more drops of blood from the patient's wound site onto the reaction area of the test sensor. When a sufficient quantity of blood is deposited on the reaction area of the test sensor, an electrochemical reaction occurs between glucose in the blood sample and the enzyme deposited on the working electrode which, in turn, produces an electrical current which decays exponentially over time. The decaying electrical current created through the chemical reaction between the enzyme and the glucose molecules in the blood sample, in turn, travels along the electrically conductive path established between the test sensor and the monitor and is measured by the microprocessor of the monitor. The microprocessor of the monitor, in turn, correlates the declining current to a standard numerical glucose value (e.g., using a scaling factor). The numerical glucose value calculated by the monitor is then shown on the monitor display for the patient to observe. In addition, the data associated with the particular blood glucose measurement is stored into the memory for the monitor.

A principal drawback associated with blood glucose monitoring systems of the type described above is that the above-described glucose measurement procedure requires multiple preparatory steps prior to each assay. Specifically, prior to performing each blood glucose measurement, a patient is required to unwrap an individual, disposable test sensor and, subsequent thereto, install the unwrapped sensor into the test port of the blood glucose test monitor. As can be appreciated, the fact that the aforementioned process fails to provide the user with a continuous means for performing multiple assays significantly increases the overall complexity and manual dexterity which is required to use such a system, which is highly undesirable.

Accordingly, it is known in the art for a multiplicity of individual test sensors to be integrated into a single sensor array. In this manner, with the sensor array properly installed into a compatible blood glucose meter, a plurality of individual tests can be performed without necessitating the user to unwrap, install and discard individual test sensors. Rather, the meter is designed to sequentially index each sensor in the array into a testing position within the meter prior to performing an individual assay. Once all of the test sensors on the sensor array have been used, the sensor array can be replaced to allow for future continuous testing.

It should be noted that sensor arrays are commonly constructed in a number of different configurations.

As an example, it is well known for sensor arrays to be constructed in the form of a disc-shaped cartridge which includes a plurality of individual test sensors that are radially arranged along its outer periphery. In this manner, with the sensor array properly installed into a compatible meter, the continuous, incremental rotation of the sensor array serves to sequentially index each successive test sensor into the proper testing position within the meter in order to perform an assay. An example of a sensor array constructed in the form of a disc-shaped cartridge is shown in U.S. Pat. No. 5,741,634 to Y. Nozoe et al.

As another example, it is well known for sensor arrays to be constructed in the form of a continuous, elongated strip which includes a plurality of individual test sensors that are linearly arranged in an end-to-end relationship. In this manner, with the sensor array properly installed into a compatible meter, the continuous, incremental linear displacement of the sensor array serves to sequentially index each successive test sensor into the proper testing position within the meter in order to perform an assay. Examples of a sensor array constructed in the form of a continuous, elongated strip are shown in U.S. Pat. No. 5,395,504 to E. Saurer et al. and U.S. Pat. No. 5,074,977 to P. W. Cheung et al.

Although useful in performing multiple continuous glucose measurements, sensor arrays of the type described above suffer from a notable drawback. Specifically, sensor arrays of the type described above are typically constructed with a limited degree of flexibility and/or bendability. Due to their relative rigidity, the sensor arrays are only capable of movement along a single plane (e.g., either through rotation or linear displacement). As a result, these types of sensor arrays often preclude design engineers from constructing a complementary meter of reduced size and/or mechanical complexity, which is highly undesirable.

SUMMARY OF THE INVENTION

It is an object of the present invention to provide a novel sensor array.

It is another object of the present invention to provide a novel sensor array which can be removably installed into a compatible analyte test monitor.

It is yet another object of the present invention to provide a sensor array of the type described above which includes a plurality of interconnected analyte test sensors.

It is still another object of the present invention to provide a sensor array of the type described above which is designed to substantially conform to a non-planar surface.

It is yet still another object of the present invention to provide a sensor array of the type described above which has a limited number of parts, which is inexpensive to manufacture and which is easy to use.

Therefore, according to one feature of the present invention, there is provided a sensor array comprising a first test sensor and a second test sensor hingedly coupled to said first test sensor.

According to another feature of the present invention, there is provided a sensor array comprising a unitary, non-conductive substrate, said substrate including a top surface and a bottom surface, a first set of electrodes deposited on the top surface of said substrate, said first set of electrodes together defining a first test sensor, and a second set of electrodes separate from said first set of electrodes, said second set of electrodes being deposited on the top surface of said substrate, said second set of electrodes together defining a second test sensor, wherein said substrate is scored.

According to another feature of the present invention, there is provided a sensor array comprising a first test sensor, a second test sensor spaced apart from said first test sensor and a unitary member coupled to said first and second test sensors.

According to another feature of the present invention, there is provided a sensor array comprising a first test sensor and a second test sensor separate from said first test sensor, wherein said first test sensor is sized and shaped to interlock with said second test sensor.

Various other features and advantages will appear from the description to follow. In the description, reference is made to the accompanying drawings which form a part thereof, and in which is shown by way of illustration, various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts:

FIGS. 8(a)-(c) depict the analyte test meter shown in FIG. 7 at various stages during its operation, the meter being shown with the sensor array shown in FIG. 1 fed thereinto, the meter being broken away in part to more clearly show the sensor array;

DETAILED DESCRIPTION OF THE PREFERRED EMBODIMENT

Figure 1:
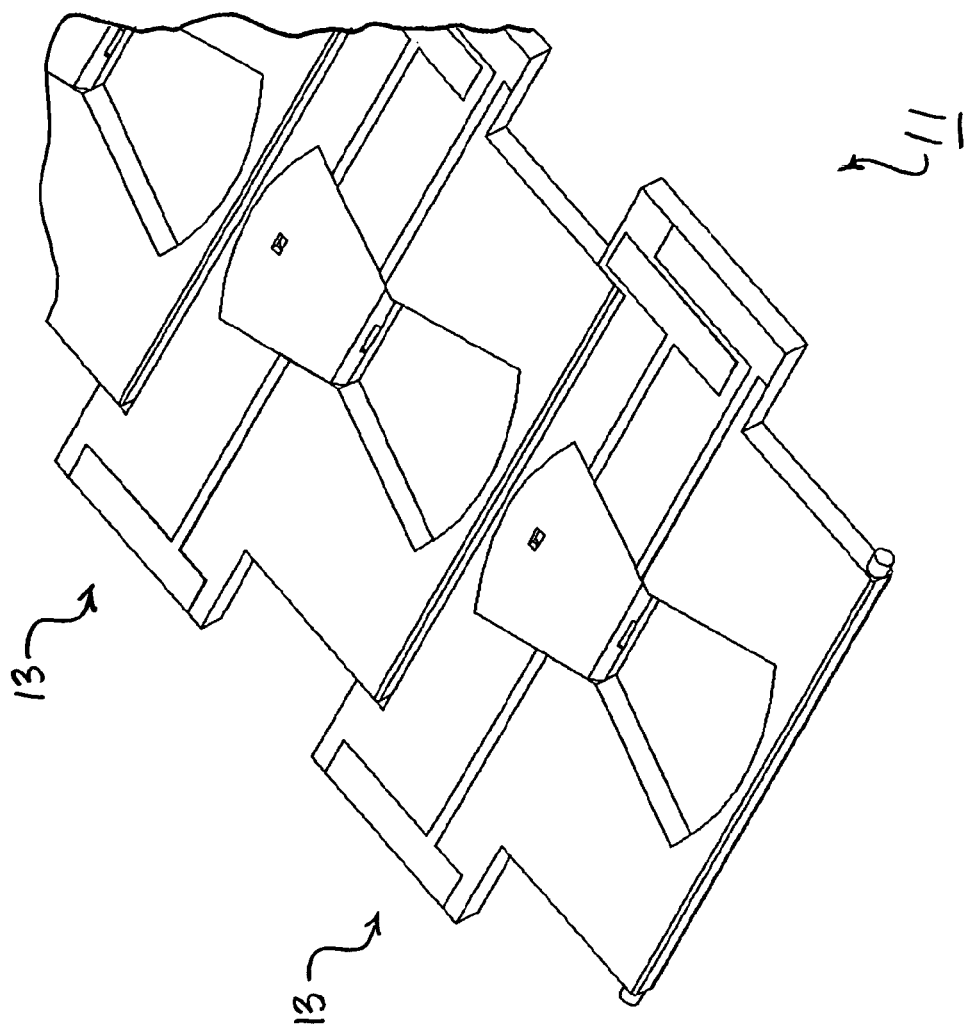
FIG. 1 is a fragmentary, top, front, right side perspective view of a first embodiment of a sensor array constructed according to the teachings of the present invention.
Figure 2:
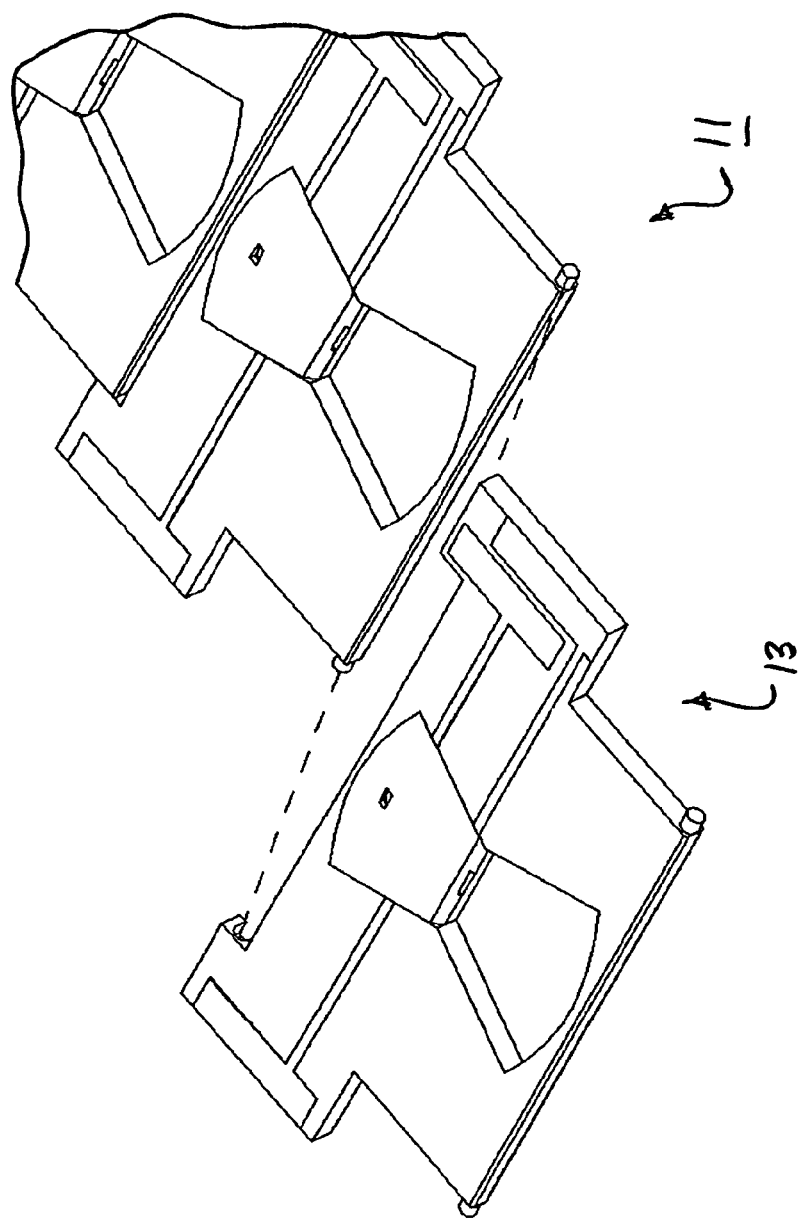
FIG. 2 is a fragmentary, top, front, right side perspective view of the sensor array shown in FIG. 1, the sensor array being shown with a single test sensor exploded therefrom.

Referring now to the drawings, there is shown in FIGS. 1-2 a first embodiment of a sensor array constructed according to the teachings of the present invention, the sensor array being identified generally by reference numeral 11. As will be described further in detail below, sensor array 11 is designed to be continuously fed into a compatible analyte test monitor. In this manner, a plurality of blood tests can be performed without requiring the user to unwrap and load individual test strips into the test monitor, which is a principal object of the present invention.

Sensor array 11 includes a plurality of individual analyte test sensors 13 which are hingedly interconnected in a front-to-back arrangement. In this manner, sensor array 11 can be configured to conform to a non-planar surface, as will be described further in detail below.

Figure 3:
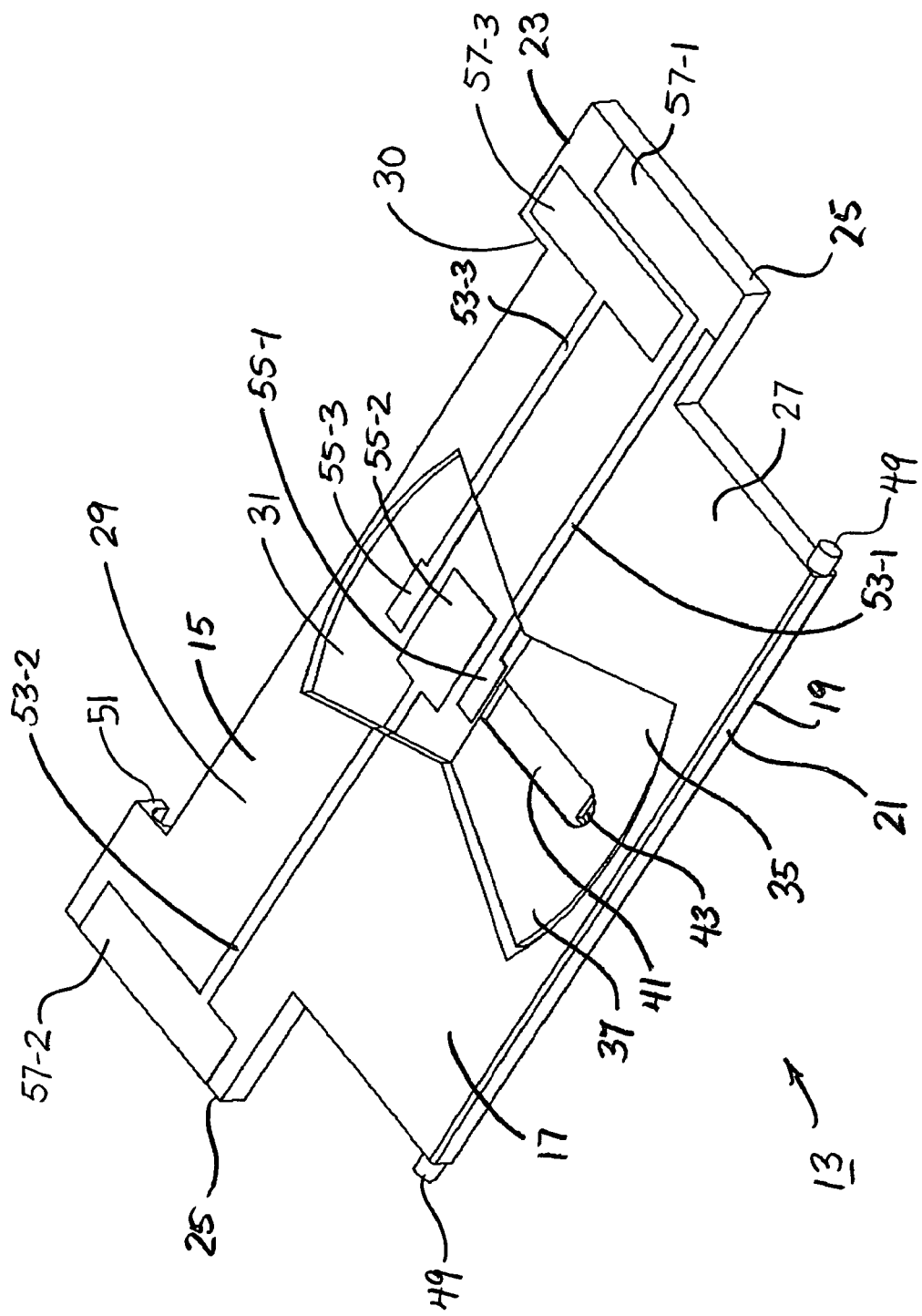
FIG. 3 is a top, front, right side perspective view of the single test sensor shown in FIG. 1, the test sensor being shown with the tab positioned within the window.
Figures 4, 5:
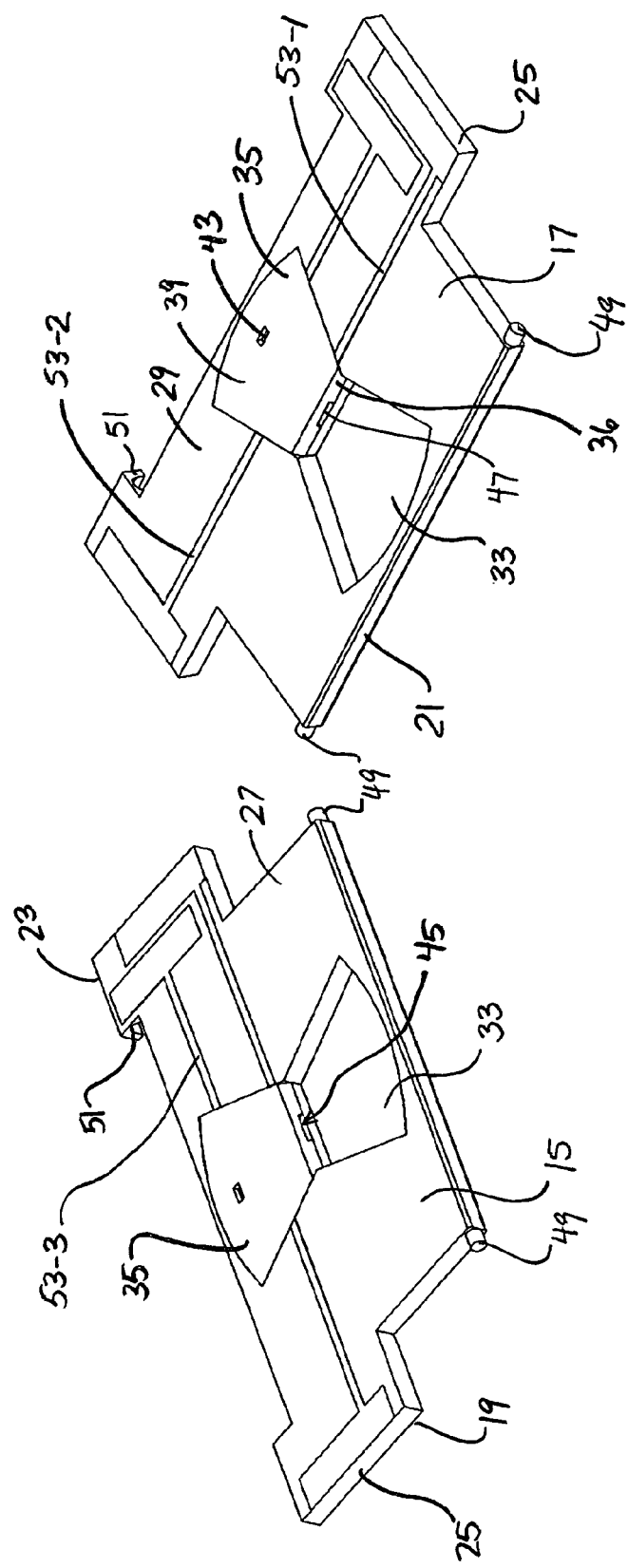
FIG. 4 is a top, front, left side perspective view of the single test sensor shown in FIG. 3, the test sensor being shown with the tab folded so as to extend into the recess in the substrate.
FIG. 5 is a top, front, right side perspective view of the single test sensor shown in FIG. 3, the test sensor being shown with the tab folded so as to extend into the recess in the substrate.

Referring now to FIGS. 3-5, each analyte test sensor 13 includes a unitary, non-conductive substrate 15 which is preferably constructed of plastic using conventional molding techniques. Substrate 15 includes a substantially flat top surface 17, a substantially flat bottom surface 19, a front edge 21, a back edge 23 and a pair of side edges 25. Substrate 15 is shaped to define a reduced-sized front portion 27 and an enlarged back portion 29, back portion 29 being longer in length than front portion 27. A laterally extending notch 30 is formed into back portion 29 along back edge 23, notch 30 being sized and shaped to fittingly receive the front portion 27 of another test sensor 13 (as seen most clearly in FIG. 1).

A fan-shaped recess 31 (shown most clearly in FIG. 3) is formed into top surface 17 of back portion 29. As will be described further below, recess 31 helps to define the reactive area for test sensor 13. Similarly, a fan-shaped window 33 (shown most clearly in FIGS. 4 and 5) is formed into front portion 27 and is sized, shaped and positioned to mirror recess 31.

Figure 6:
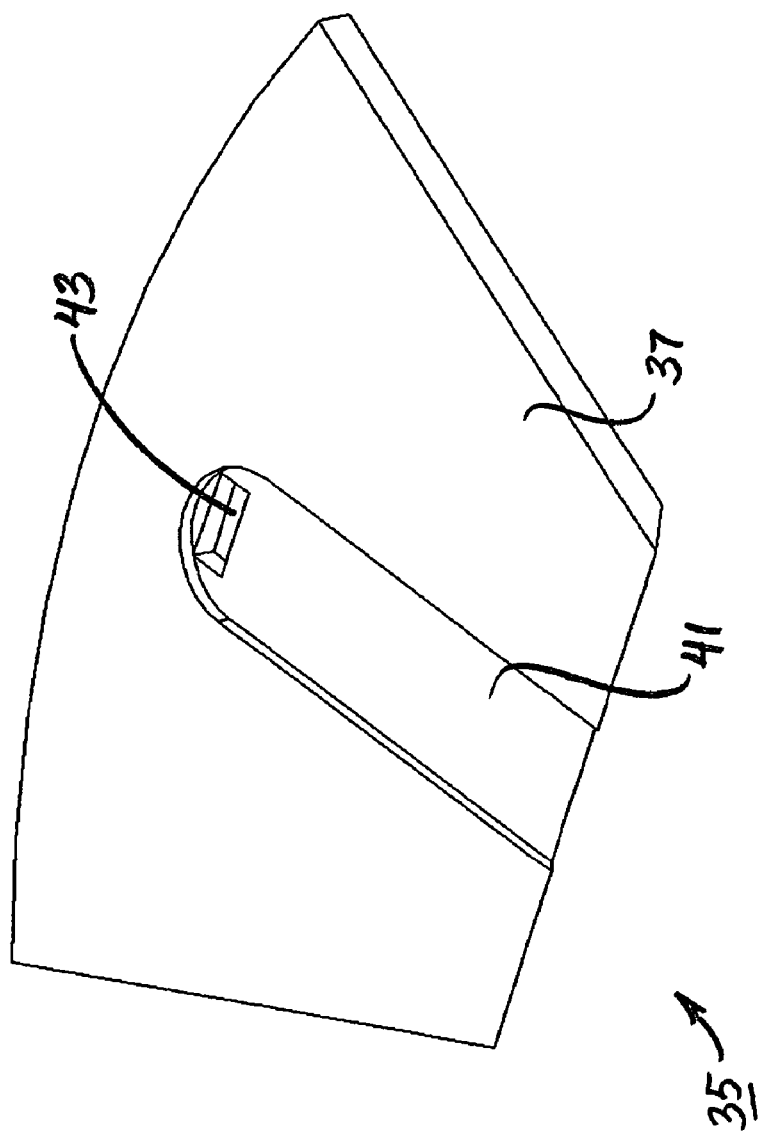
FIG. 6 is an enlarged, top, rear perspective view of the tab shown in FIG. 3.

A tab 35, which is preferably constructed of a thin, transparent, molded plastic material, is connected to substrate 15 along one of its edges 36. Preferably, test sensor 13 is manufactured with tab 35 orientated to fittingly protrude within window 33, as seen most clearly in FIG. 3. Tab 35 (shown in isolation in FIG. 6) includes a substantially flat top surface 37 and a substantially flat bottom surface 39. A shallow groove 41 is formed into top surface 37. In addition, a vent hole 43 is formed in tab 35 within groove 41.

As seen most clearly in FIGS. 4 and 5, folding tab 35 about connected edge 36 causes tab 35 to fittingly protrude into recess 31 (with top surface 37 facing down into recess 31 and with bottom surface 39 substantially flush with top surface 17 of substrate 15). It should be noted that, when tab 35 is folded about connected edge 36, groove 41 serves to create a substantially enclosed blood channel 45 which extends laterally across recess 31. As will be described further below, test sensor 13 is designed such that blood can enter into blood channel 45 through an open end 47 formed along connected edge 36. With blood entered into channel 45, vent hole 43 serves to draw the blood across the reactive area for test sensor 13, thereby providing test sensor 13 with an adequate blood sample with which to conduct an assay.

A pair of opposing pins 49 are formed onto side edges 25 proximate front edge 21, each pin 49 being generally cylindrical in construction and extending orthogonally out from its corresponding side edge 25.

In addition, a pair of sockets 51 are formed into back edge 23 within notch 30. Each socket 51 preferably has a key-hole shape in lateral cross-section and is sized and shaped to receive a corresponding pin 49 from another test sensor 13. In this manner, each socket 51 is sized and shaped such that a corresponding pin 49 can be releasably inserted thereinto (e.g., through a press-fit or snap-fit engagement). As a result, individual test sensors 13 can be hingedly interconnected to and/or separated from the remainder of sensor array 11 as needed.

It should be noted that adjacent test sensors 13 need not be releasably interconnected. Rather, it is to be understood that adjacent test sensors 13 could be permanently coupled together without departing from the spirit of the present invention.

It should also be noted that sensor array 11 need not be limited to a pin and socket means of hinged interconnection between adjacent test sensors 13. Rather, it is to be understood that adjacent test sensors 13 could be coupled together by any other similar hinged connection means (e.g., ball and socket or living hinge) without departing from the spirit of the present invention.

It should further be noted that adjacent test sensors 13 need not be interconnected in a front-to-back arrangement. Rather, it is to be understood that adjacent test sensors 13 could be hingedly interconnected in alternative arrangements (e.g., in a side-to-side relationship) without departing from the spirit of the present invention.

A pair of carbon-layer electrodes 53-1 and 53-2 are deposited onto back portion 29 of substrate 15 along a portion of its length in a spaced-apart relationship, electrode 53-1 serving as the reference electrode for test sensor 13 and electrode 53-2 serving as the working electrode for test sensor 13. An optional third electrode 53-3 may be provided which serves as the trigger electrode for test sensor 13 (i.e., an electrode which measures whether an adequate blood sample has been deposited within the reactive area for test sensor 13 to function properly).

Each electrode 53 is deposited onto substrate 15 in any conventional manner (e.g., screen printing) and includes a first end 55 and a second end 57. First end 55 of each electrode 53 is located within recess 31 (i.e., within the reactive area for test sensor 13). Second end 57 of each electrode 53 is located along either side edge 25 and in a manner suitable for connection with the compatible test meter. An enzyme (not shown) which produces an electrical reaction when exposed to a particular analyte (e.g., glucose) is applied to first end 55-2 of working electrode 53-2 (i.e., within the reactive area).

In order to measure the concentration of a particular analyte in a patient's blood, the patient is required to deposit a blood sample into through open end 47 of blood channel 45. The blood sample, in turn, is drawn (i.e., pulled) into blood channel 45 by means of capillary action (created by vent hole 43) and ultimately across first end 55 of electrodes 53 (i.e., within the reactive area). Simultaneously, a voltage provided by the compatible analyte test monitor is applied across second end 57 of electrodes 53-1 and 53-2, the conductive nature of the blood sample serving to effectively create a closed circuit between first end 55-1 of reference electrode 53-1 and first end 55-2 of working electrode 53-2. The application of the blood sample onto the enzyme deposited on first end 55-2 of working electrode 53-2 creates an electrical reaction. In response to said reaction, a current (commonly referred to in the art as the working current) is produced which travels along working electrode 53-2 (from first end 55-2 to second end 57-2), the value of said working current being directly related to the concentration of the particular analyte in the blood sample. Accordingly, with sensor array 11 properly loaded into the compatible analyte test meter, the meter is capable of measuring the value of the working current along working electrode 53-2 and, in turn, using said value to calculate the analyte concentration in the blood sample (e.g., by multiplying said value by a scaling factor).

It should be noted that test sensor 13 is not limited to the use of electrochemical means for determining the concentration of a particular analyte in a blood sample. Rather, it is to be understood that test sensor 13 could use alternative conventional means (e.g., photochemical means) to calculate the concentration of a particular analyte in a blood sample without departing from the spirit of the present invention.

As noted briefly above, the fact that sensor array 11 includes a plurality of interconnected test sensors 13 enables the user to perform a multitude of individual tests without the need to unwrap, load and discard individual test sensors 13. Rather, by indexing the continuous chain of test sensors 13 through the meter in defined increments, multiple individual tests can be performed with requiring the user to undertake any preparatory steps (e.g., unwrapping, loading, unloading and/or discarding individual test sensors), which is highly desirable.

Furthermore, the hinged interconnection of test sensors 13 enables sensor array 11 to be configured to substantially conform to a non-planar surface. In this manner, sensor array 11 can be fed into and indexed through the meter along a curved surface which, in turn, provides engineers with a broader range of possible meter designs, which is highly desirable.

It should be noted that sensor array 11 is designed to operate with a modified version of the SOF-TACT™ blood glucose meter which is manufactured and sold by Abbott Laboratories, Medisense Products of Bedford, Mass. and which is represented, inter alia, in U.S. Pat. No. 6,506,168, which is incorporated herein by reference. However, it is to be understood that sensor array 11 is not limited in its compatibility with the aforementioned modified version of the SOF-TACT™ blood glucose meter. Rather, it is to be understood that sensor array 11 could be used with various types of blood glucose test meters without departing from the spirit of the present invention.

The existing SOF-TACT™ blood glucose meter is adapted to receive both a single disposable lancet and a single disposable test strip. In order to prepare the meter for an assay, the patient is required to open a pivotally mounted cover. With the cover opened, the patient is required to unwrap an individually sealed lancet and, in turn, mount the unwrapped lancet in a cylindrical lancet holder. In addition, the patient is required to unwrap an individually sealed test strip and, in turn, insert the unwrapped test strip into a test strip port. With a lancet and a test strip installed into the meter as described above, the cover is pivoted closed. To commence an assay, the patient positions a specified region of the monitor against his/her skin and presses an activation button. Depression of the activation button creates a pressure gradient which drives the lancet through an opening in the pivotable cover and into the patient's skin. The pressure gradient is then removed which retracts the lancet to its original unfired position.

After an opening has been formed in the skin of the patient, the blood sample is collected so that an assay can be performed. Specifically, a vacuum pump is used to draw blood from the wound site and in the direction towards the test strip. Simultaneously, mechanical linkages within the monitor use pressure to move the test strip towards the opening in the pivotable cover such that blood emerging from the patient's skin collects onto the reaction area of the test strip. When a sufficient amount of blood has been collected, the vacuum pump is deactivated. The meter then performs the assay based upon the electrochemical signal generated by the test strip and displays the result on an LCD screen.

Upon completion of the assay, the user is required to pivot open the cover of the meter and remove the used test strip and lancet. Because each test strip and lancet is designed for a single-use, the used test strip and lancet are discarded. The cover is then closed until future tests are required, at which time, the above-described process is repeated.

Although the existing SOF-TACT™ blood glucose meter effectively combines both lancing and measurement processes into a single device, the user is still required to store, unwrap, load and discard a conventional analyte test strip into the meter prior to each use, thereby rendering this system somewhat labor intensive and complicated to use.

Figure 7:
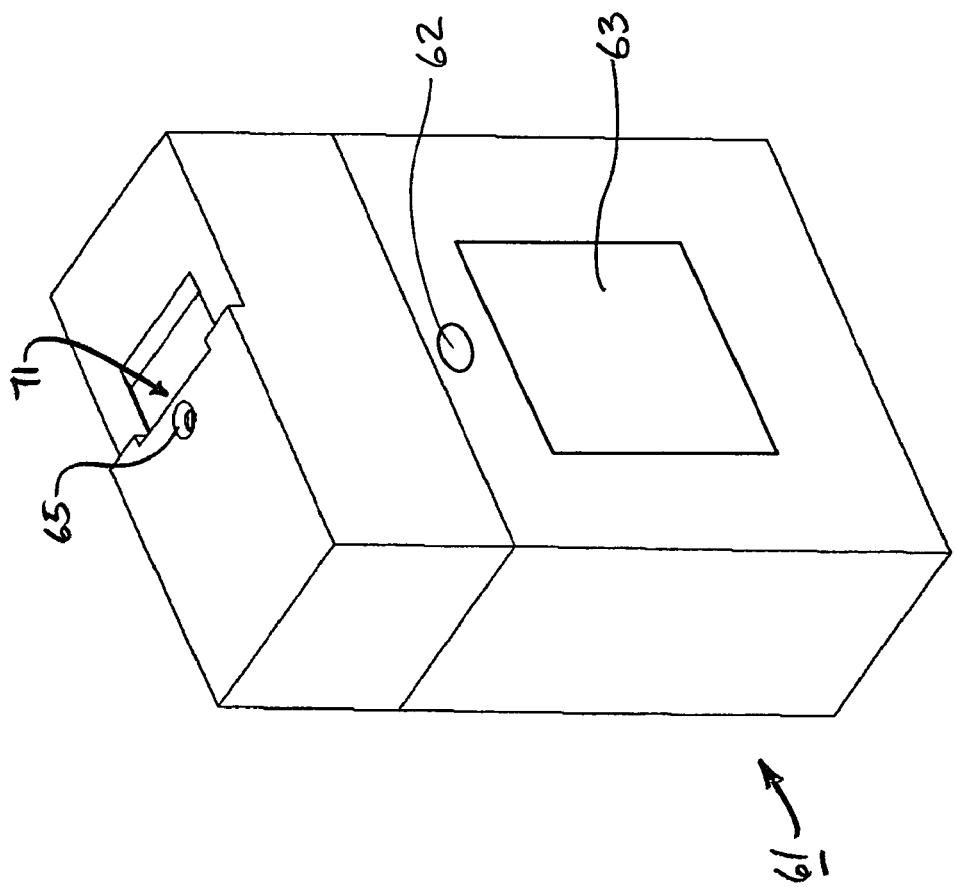
FIG. 7 is a perspective view of an analyte test meter with which the sensor array shown in FIG. 1 is compatible.

Accordingly, referring now to FIG. 7, there is shown a modified version of the SOF-TACT™ blood glucose meter (said meter being represented generally by reference numeral 61) which is specifically designed to operate using sensor array 11. Meter 61 preferably includes an actuation button 62 for controlling the operation of meter 61 and a LCD screen 63 for displaying test results.

Figure 8A:
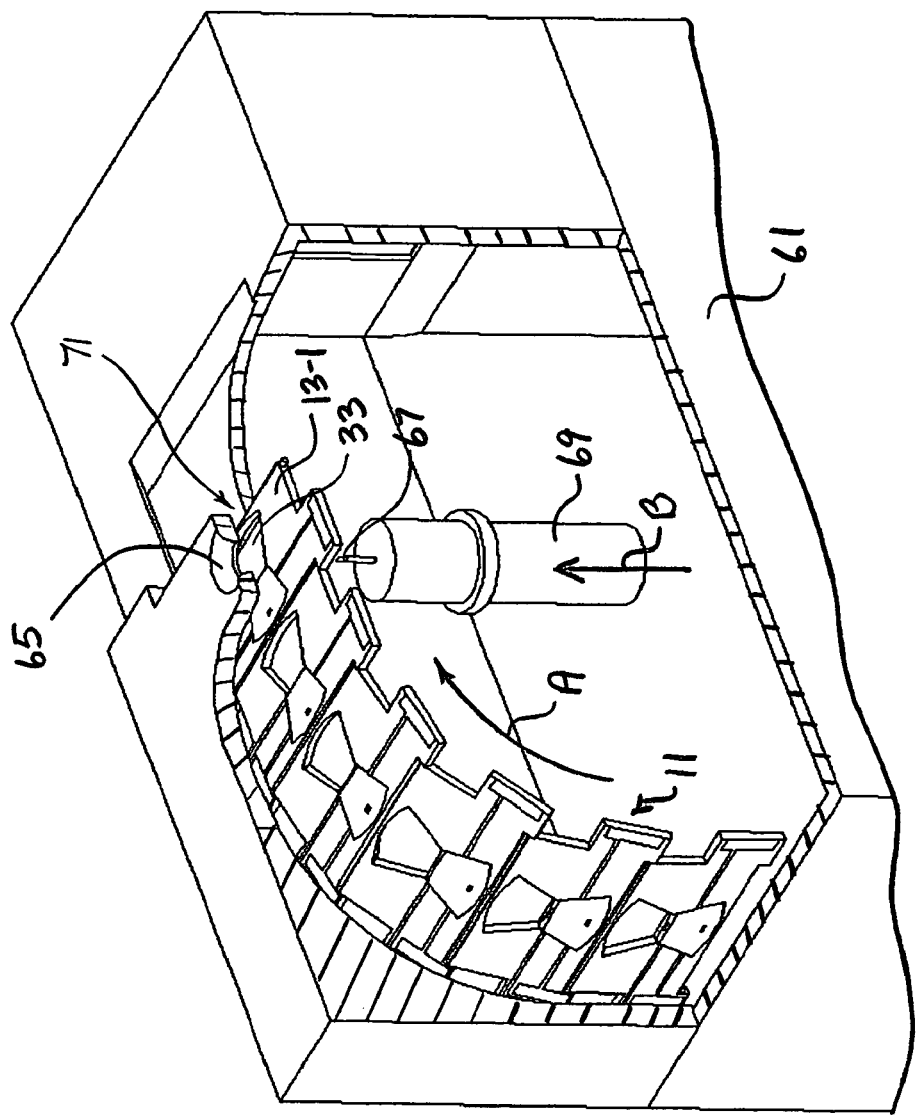
Figure 8A:
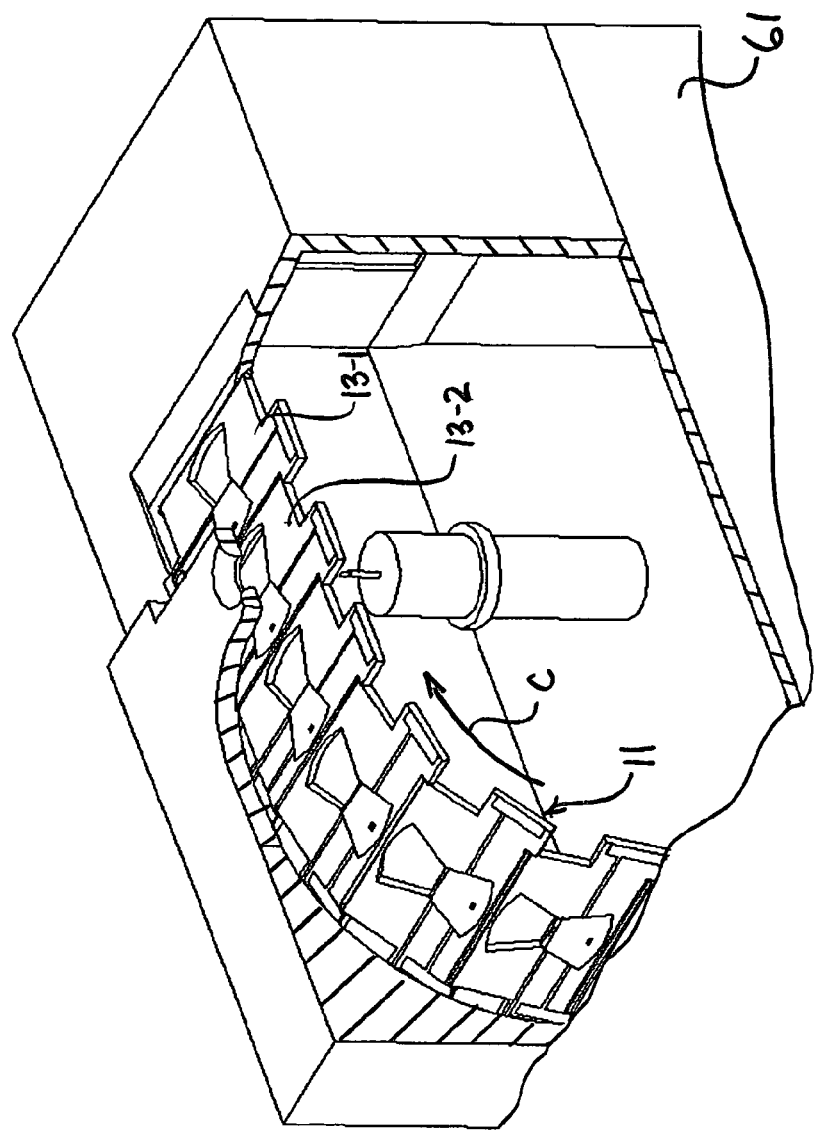
Figure 8C:
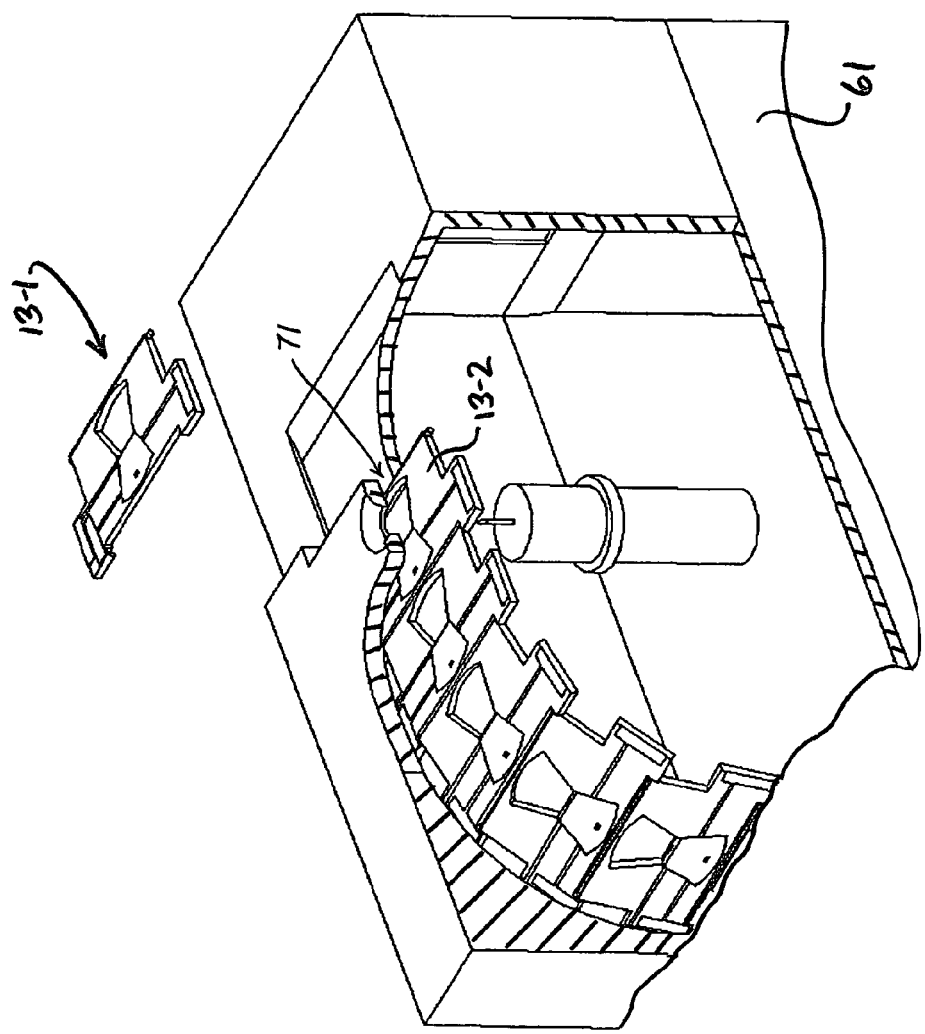

Referring now to FIGS. 8(a)-(c), meter 61 is designed to receive sensor array 11 in the following manner in order to continuously perform a series of blood glucose measurements. First, sensor array 11 is removed from any protective wrapping. Once unpackaged, sensor array 11 is loaded by the patient into meter 61. Mechanical linkages (not shown) within meter 61 serve to automatically index sensor array 11 along an arcuate feed track (not shown). As noted above, due to the hinged interconnection between successive test sensors 13, sensor array 11 is able to substantially conform to the arcuate feed track within meter 61, which is highly desirable.

As shown in FIG. 8(*a*), meter 61 indexes sensor array 11 along the curved path (in the direction represented by arrow A) until the leading test sensor 13-1 is aligned in the proper position for meter 61 to perform its lancing operation. Specifically, the leading test sensor 13-1 is positioned such that its window 33 aligns directly beneath a skin distension cup 65 and directly above the sharpened tip 67 of a lancet 69 which has been installed into meter 61. With the leading test sensor 13-1 positioned as such, second ends 57 of electrodes 53 for leading test sensor 13-1 are drawn into direct contact with conductive leads (not shown) in meter 61, thereby establishing a current path between the leading test sensor 13-1 and the central processing unit (CPU) of monitor 61. With a current path established between test sensor 13-1 and monitor 61, monitor 61 can notify the user (e.g., using screen 63) that the system is ready to perform a blood test.

In order to perform an blood test, the patient is required to dispose the desired test site (e.g., the patient's finger) against skin distension cup 65. As can be appreciated, application of the desired test site against cup 65 serves to distend and bulge the patient's skin, thereby causing the patient's imminent wound site to be replete with blood. With the patient's skin disposed against cup 65 in this manner, the firing mechanism for monitor 61 is activated (e.g., by depressing externally accessible activation button 62).

Activation of the firing mechanism causes lancet 69 to be driven linearly upward (as represented by arrow B in FIG. 8(*a*)) such that sharpened tip 67 passes through window 33 and, in turn, penetrates into the patient's skin. Immediately thereafter, lancet 69 is retracted. Upon retraction of lancet 69, blood exits the wound site in the patient's skin and is funneled down through cup 65 (e.g., using gravitational and/or vacuum forces).

At this time, meter 61 continues to index sensor array 11 in the direction of arrow A. As sensor array 11 is indexed, second ends 57 of electrodes 53 in leading test sensor 13-1 remain in direct contact with conductive leads (not shown) in meter 61. Furthermore, the indexing of sensor array 11 draws blood into blood channel 45 of leading test sensor 13-1 through open end 47. Once an adequate blood sample has reached the reactive area of test sensor 13-1 (i.e., activating trigger electrode 53-3), monitor 61 then measures the working current present along working electrode 53-2 (the working current resulting from the reaction between the enzyme present on electrode 53-2 and the blood sample applied thereto). Once monitor 61 measures the working current, the CPU calculates the concentration of the analyte in the blood sample using the working current (e.g., by multiplying the working current by a known scaling factor). The results of said calculation are preferably shown on screen 63.

Upon completion of the assay, meter 61 recommences its indexing of sensor array 11 (in the direction of arrow C in FIG. 8(*b*)) until the used test sensor 13-1 passes through an exit slot 71 in meter 61. With sensor array 11 indexed as such, the next successive test sensor 13-2 is disposed in proper position for an additional lancing operation (i.e., to perform another test). In this manner, a continuous process for conducting blood glucose measurements is achieved.

It should be noted that, because the used test sensor 13-1 has been expelled through exit slot 71, the user is able to separate the used test sensor 13-1 from the remainder of sensor array 11, as shown in FIG. 8(*c*). In this manner, used test sensor 13-1 can be immediately discarded after its use, which is highly desirable.

As noted above, numerous modifications could be made to sensor array 11 without departing from the spirit of the present invention. For example, it is to be understood that sensor array 11 could modified to include alternative means for hingedly connecting successive test sensors 13 without departing from the spirit of the present invention, as will be described further in detail below.

Figure 9A:
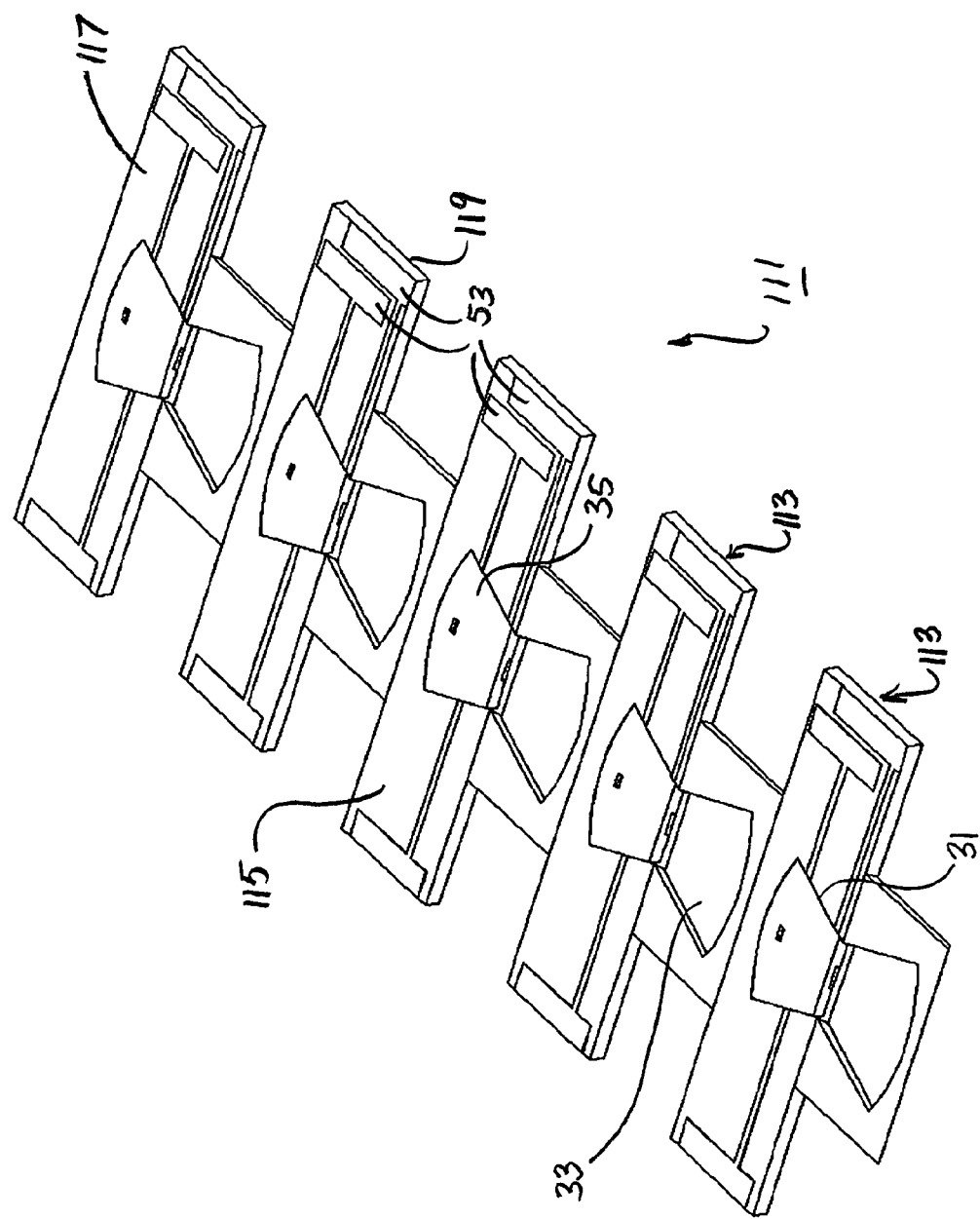
FIGS. 9(a) and 9(b) are top perspective and right side plan views, respectively, of a second embodiment of a sensor array constructed according to the teachings of the present invention.
Figure 9B:
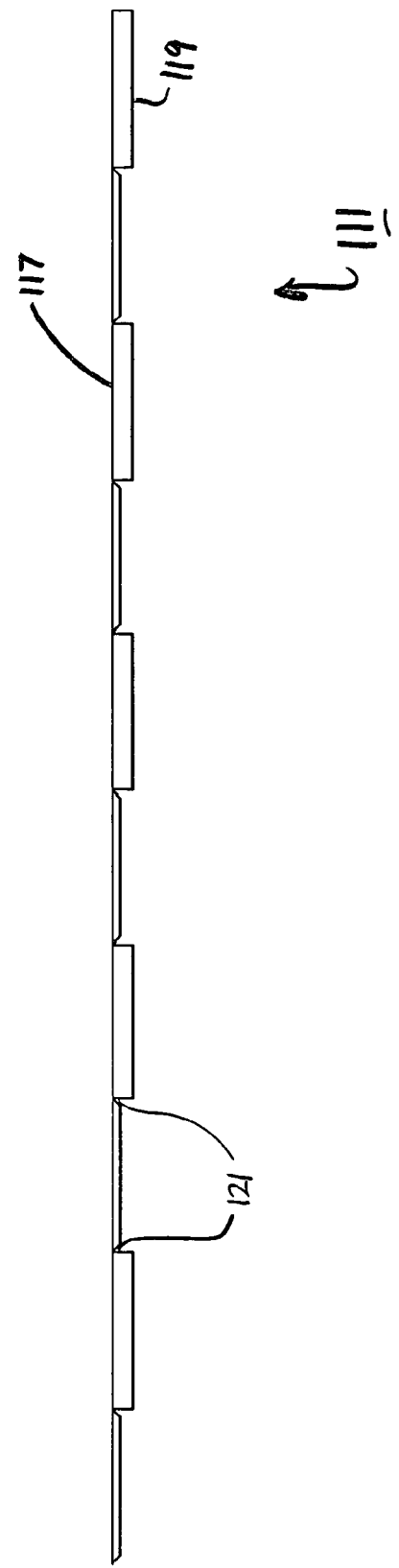

Referring now to FIGS. 9(*a*) and 9(*b*), there is shown a second embodiment of a sensor array which is constructed according to the teachings of the present invention, the sensor array being identified generally by reference numeral 111. Sensor array 111 is similar to sensor array 11 in that sensor array 111 includes a plurality of test sensors 113 which are arranged in a front-to-back arrangement. However, sensor array 111 differs from sensor array 11 in the manner in which test sensors 113 are interconnected.

Specifically, sensor array 111 includes a one-piece, non-conductive substrate 115 which is common to each of the test sensors 113. Substrate 115, which is preferably constructed of plastic using conventional molding techniques, includes a substantially flat top surface 117 and a bottom surface 119.

Substrate 115 is scored at multiple locations to enable sensor array 111 to bend. As seen most clearly in FIG. 9(*b*), a plurality of laterally extending lines of weakness 121 are formed into substrate 115, each line of weakness 121 represented herein as being in the form of a notch which is triangular in lateral cross-section and which is formed into and extends linearly across bottom surface 119. As can be appreciated, each line of weakness 121 serves as a fold line about which substrate 115 can be bent so as to enable sensor array 111 to adequately conform to a non-planar surface.

However, it should be noted that line of weakness 121 is not limited to being in the form of a notch which is triangular in lateral cross-section and which is formed into and extends linearly across bottom surface 119. Rather, it is to be understood that line of weakness 121 could differ in lateral cross-section (e.g., U-shaped in lateral cross-section or in the form of a line of perforation) without departing from the spirit of the present invention. In addition, it is to be understood that line of weakness 121 could extend in a non-linear manner (e.g., in a curved or jagged manner) without departing from the spirit of the present invention. Furthermore, line of weakness 121 could be formed in top surface 117 (rather than bottom surface 119) without departing from the spirit of the present invention.

Lines of weakness 121 preferably extend across substrate 115 at fixed intervals. It should be noted that the number of lines of weakness 121 for sensor array 111 could be modified without departing from the spirit of the present invention. In fact, increasing the number of lines of weakness 121 (i.e., decreasing the spacing between successive lines) would serve to improve the ability of array 111 to conform to an arcuate surface.

Preferably, a line of weakness 121 extends laterally across substrate 115 at the approximate junction point between adjacent test sensors 113. In this manner, these lines of weakness 121 may ultimately serve as a cut line through which used test sensors 113 are separated from the remainder of sensor array 111.

Test sensor 113 is similar in construction to test sensor 13 in that each test sensor 113 includes a fan-shaped recess 31 formed into top surface 117, a fan-shaped window 33 formed into substrate 115 and a tab 35 connected to substrate 115 which is sized and shaped to fittingly protrude into window 33. In addition, each test sensor 113 includes a plurality of carbon-layer electrodes 53 deposited onto substrate 115 in a spaced-apart relationship. As can be appreciated, each test sensor 113 functions in a substantially similar manner to test sensor 13 when used to perform an assay.

Figure 10:
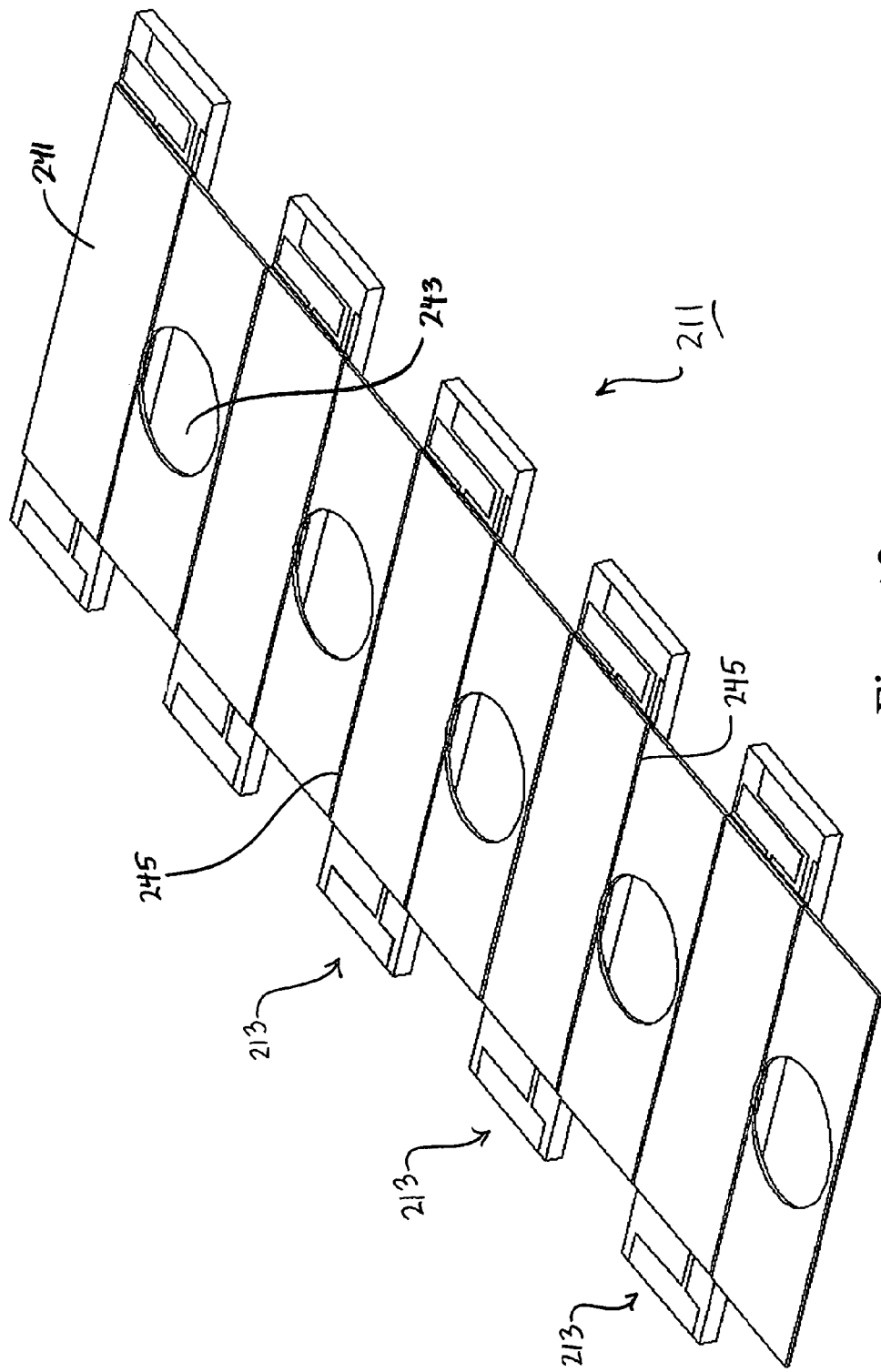
FIG. 10 is a top, front, right side perspective view of a third embodiment of a sensor array constructed according to the teachings of the present invention.
Figure 11:
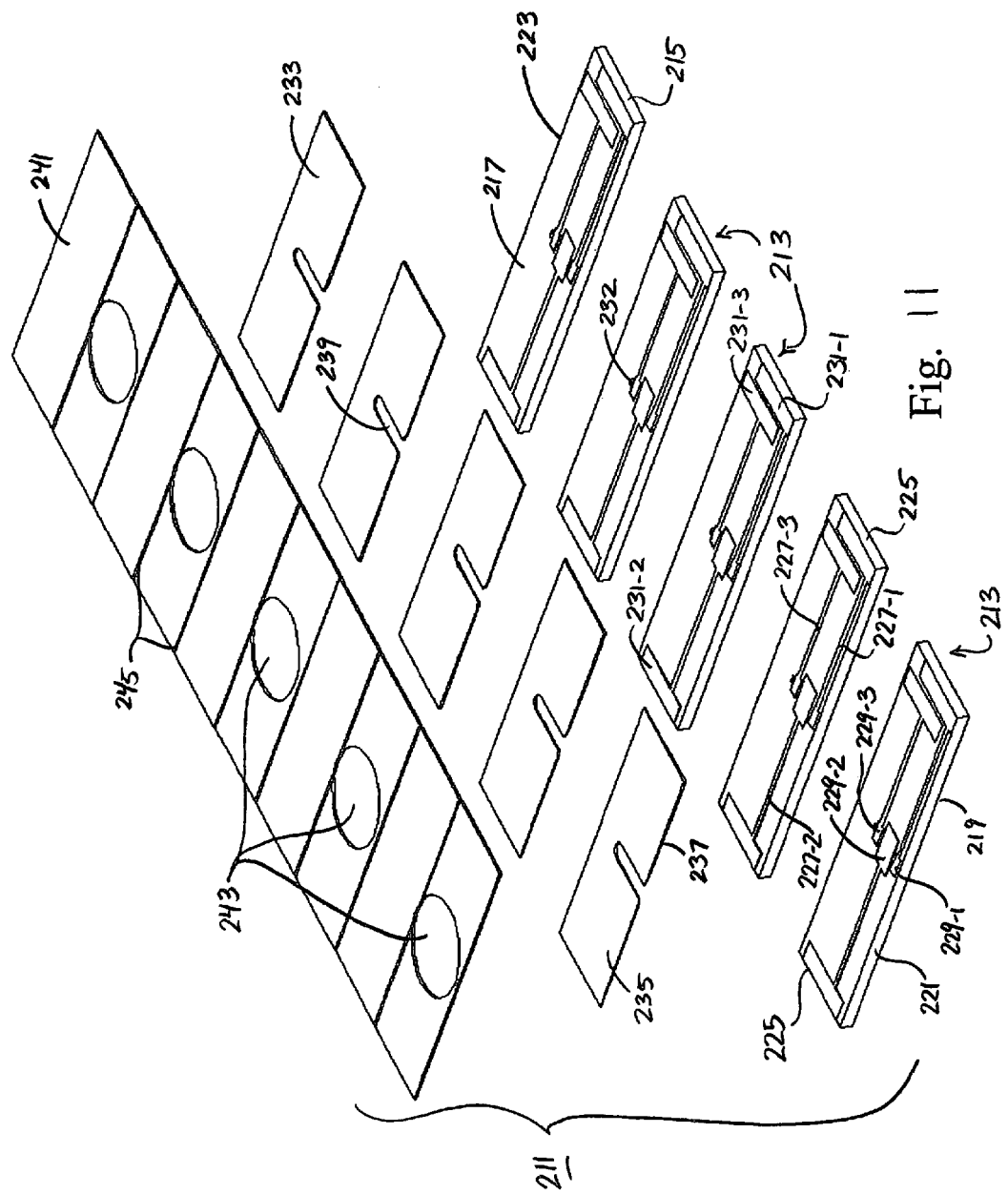
FIG. 11 is an exploded, top, front, right side perspective view of the sensor array shown in FIG. 10.

Referring now to FIGS. 10 and 11, there is shown a third embodiment of a sensor array which is constructed according to the teachings of the present invention, the sensor array being identified generally by reference numeral 211. Sensor array 211 includes a plurality of individual test sensors 213 which are spaced apart from one another and are configured in a parallel, front-to-back arrangement.

Each test sensor 213 includes a unitary, non-conductive substrate 215 which is preferably constructed of plastic using conventional molding techniques. Substrate 215 is preferably in the form of a thin, rectangular strip which includes a substantially flat top surface 217, a substantially flat bottom surface 219, a front edge 221, a back edge 223, and a pair of side edges 225. However, it is to be understood that the particular shape of substrate 215 could be modified without departing from the spirit of the present invention.

A pair of carbon-layer electrodes 227-1 and 227-2 are deposited onto top surface 217 along a portion of its length in a spaced-apart relationship, electrode 227-1 serving as the reference electrode for test sensor 213 and electrode 227-2 serving as the working electrode for test sensor 213. An optional third electrode 227-3 may be provided which serves as the trigger electrode for test sensor 213.

Each electrode 227 is deposited onto substrate 213 in any conventional manner (e.g., screen printing) and includes a first end 229 and a second end 231. First end 229 of each electrode 227 is located towards the center of top surface 217 and together define a reactive area for test strip 213. Second end 231 of each electrode 227 is located along either side edge 225 and in a manner suitable for connection with a compatible test meter. An enzyme (not shown) which produces an electrical reaction when exposed to a particular analyte (e.g., glucose) is applied to second end 231 of working electrode 227-2.

It should be noted that a small rectangular vent hole 232 (seen most clearly in FIG. 13) extends vertically through each substrate 215 from top surface 217 to bottom surface 219. Vent hole 232 is located directly behind first end 229-3 of trigger electrode 227-3 and serves to facilitate in drawing blood into the reaction area for test sensor 213, as will be described further below.

A thin, rectangular spacer 233 is mounted onto each test sensor 213. Spacer 233 includes a substantially flat top surface 235 and a substantially flat bottom surface 237. Bottom surface 237 of spacer 233 is preferably disposed over electrodes 227 and is secured to test strip 213 using an adhesive. Each spacer 233 is additionally shaped to define a narrow slot 239 which extends laterally along a portion of its length, the function of slot 239 to become apparent below. It should be noted that one end of slot 239 extends to the outer periphery of spacer 233.

An elongated, unitary member 241 is mounted laterally across each spacer 233 and is retained thereagainst using an adhesive. Unitary member 241 is preferably constructed of a thin, highly flexible plastic material and is shaped to define a plurality of circular openings 243.

Unitary member 241 is also scored at multiple locations. As seen most clearly in FIG. 12, a plurality of laterally extending lines of weakness 245 are formed into flexible unitary member 241 in a spaced apart relationship. Each line of weakness 245 is represented herein as including a pair of mirror image V-shaped notches, one notch being formed into the top surface of flexible member 241 and the other notch being formed into the bottom surface of flexible member 241. However, it is to be understood that the particular lateral cross-section of each line of weakness 245 could be modified without departing from the spirit of the present invention.

Together, the highly flexible nature of member 241 as well as the plurality of laterally-extending lines of weakness 245 enables unitary member 241 to substantially bend which, in turn, enables sensor array 211 to more closely conform to a curved surface, which is a principal object of the present invention.

Figure 12:
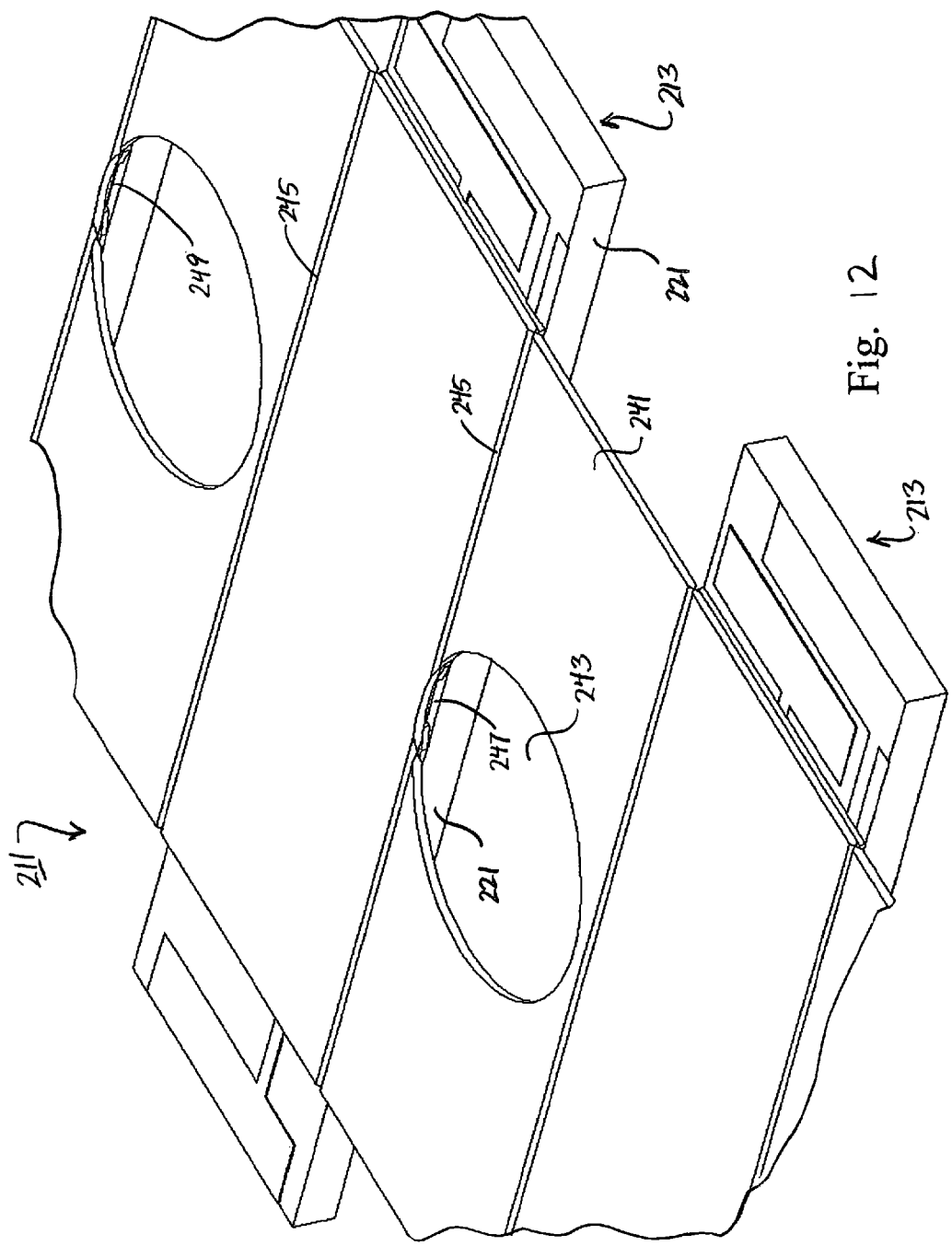
FIG. 12 is an enlarged, fragmentary, top, front, right side perspective view of the sensor array shown in FIG. 10.
Figure 13:
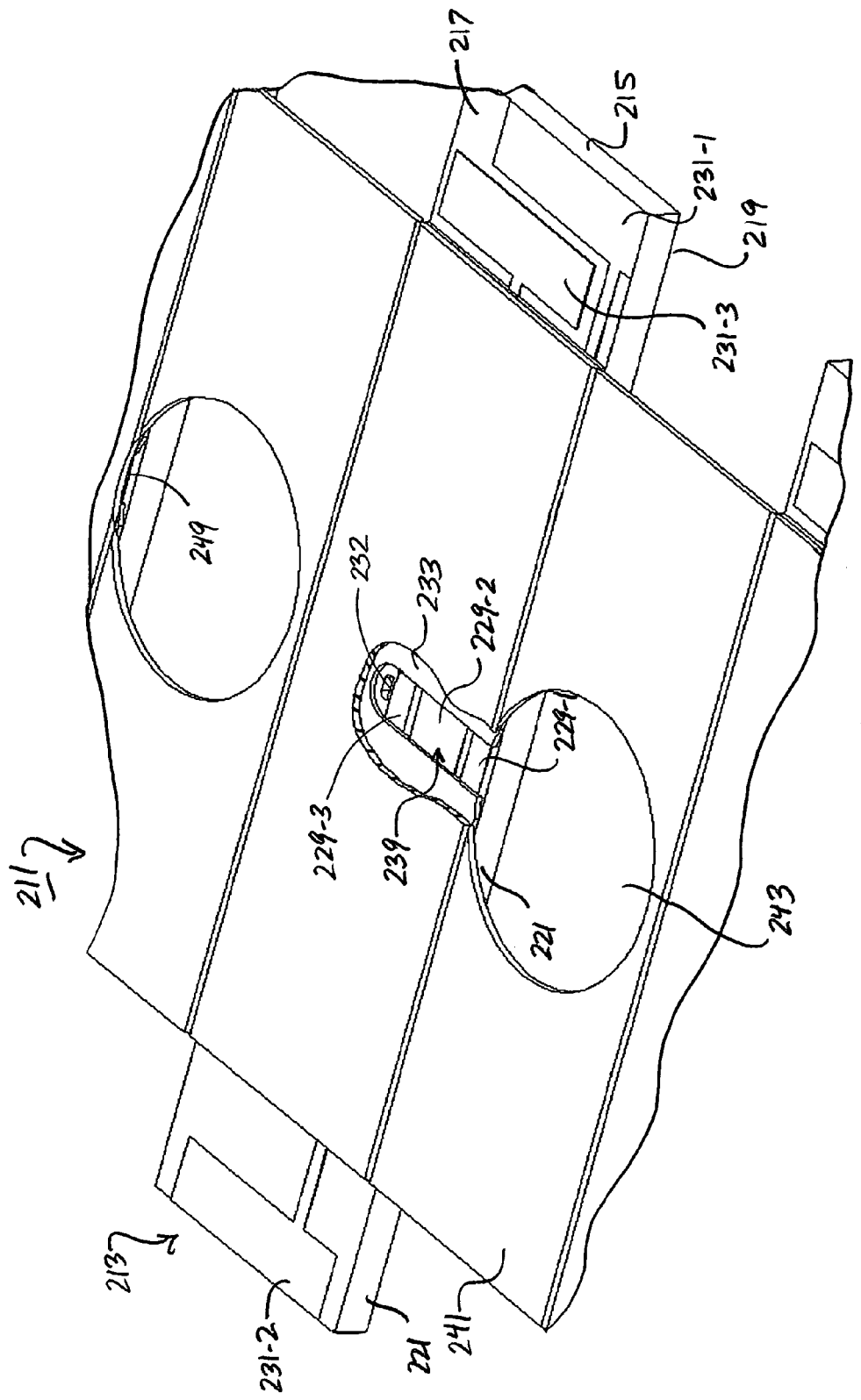
FIG. 13 is an enlarged, fragmentary, top, front, right side perspective view of the sensor array shown in FIG. 10, the unitary flexible member being shown broken away in part to more clearly show the blood channel for a test sensor.

As seen most clearly in FIGS. 12 and 13, with sensor array 211 in its assembled form, front edge 221 of each sensor 213 extends tangentially to a corresponding hole 243. In addition, each slot 239 extends laterally across the reactive area of sensor 213. In this manner, slot 239 creates a substantially enclosed blood channel 247 which includes an open blood entryway 249. In order for test sensor 213 to conduct an assay, a blood sample is deposited into blood channel 247 through entryway 249 and is drawn inward toward the reactive area by its corresponding vent hole 232, which is in alignment with channel 247 (as seen in FIG. 13). With blood deposited in the reactive area, each test sensor 213 operates in a similar manner in which test sensor 13 operates (as described in detail above).

It should be noted that array 211 is not limited to the use of spacers 233 to create blood channels 247. Rather, it is to be understood that blood channels 247 could be provided by modifying the construction of test sensor 213 (e.g., by recessing top surface 217 of substrate 215 in the reaction area) or flexible member 241 (e.g, by forming a recess in its underside), thereby enabling spacers 233 to be eliminated from array 211 without departing from the spirit of the present invention.

It should also be noted that although vent holes 232 are shown herein as being formed in substrate 215, it is to be understood that vent holes 232 could alternatively be formed in member 241 without departing from the spirit of the present invention.

It should further be noted that member 241 need not meet both of the following criteria: (1) that it be constructed of a flexible material and (2) that it include laterally extending lines of weakness 245. Rather, it is to be understood that member 241 could meet only one of the two aforementioned criteria (so as to enable member 241 to still sufficiently flex) without departing from the spirit of the present invention.

Figure 14:
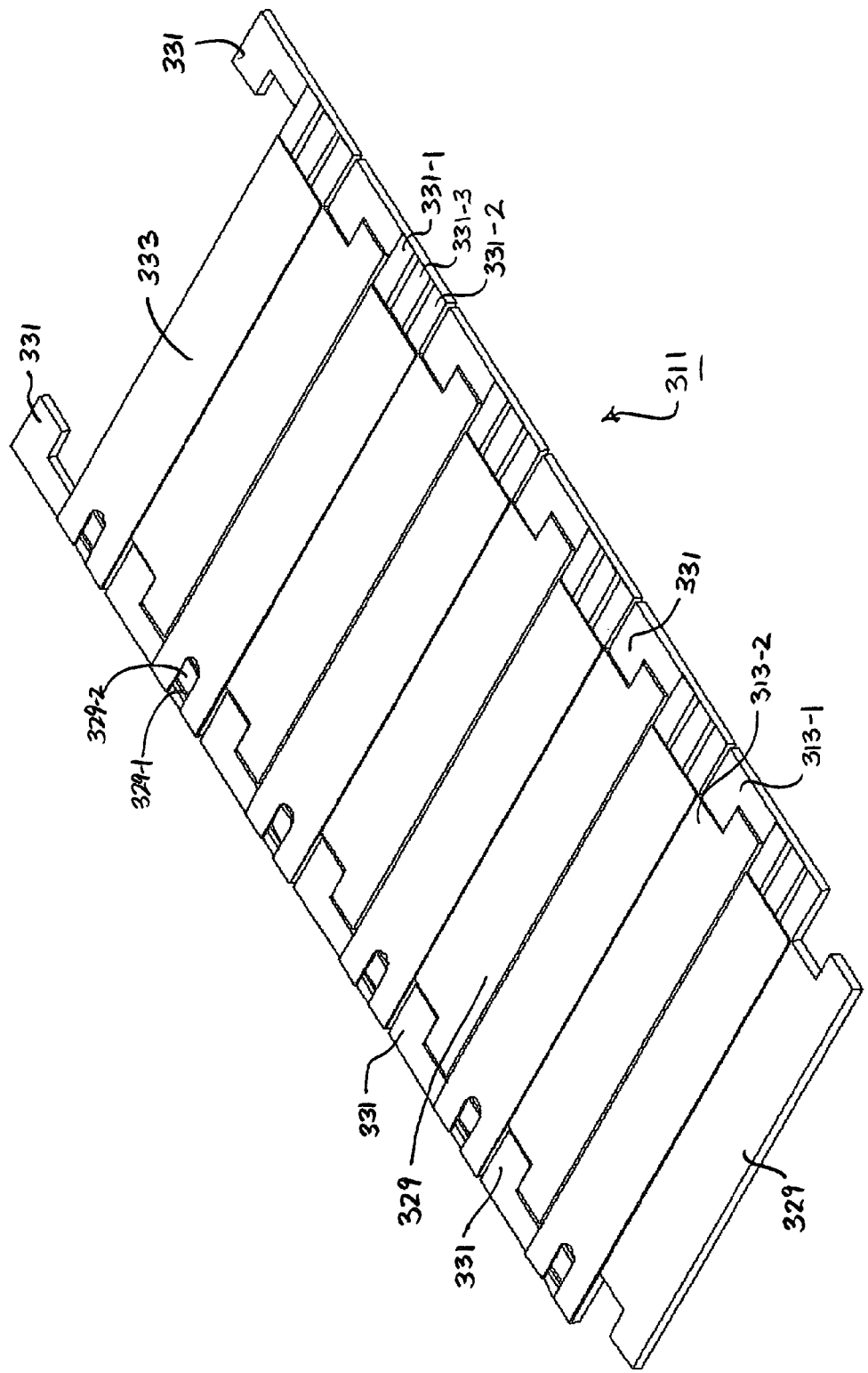
FIG. 14 is top, front, right side perspective view of a fourth embodiment of a sensor array constructed according to the teachings of the present invention.
Figure 15:
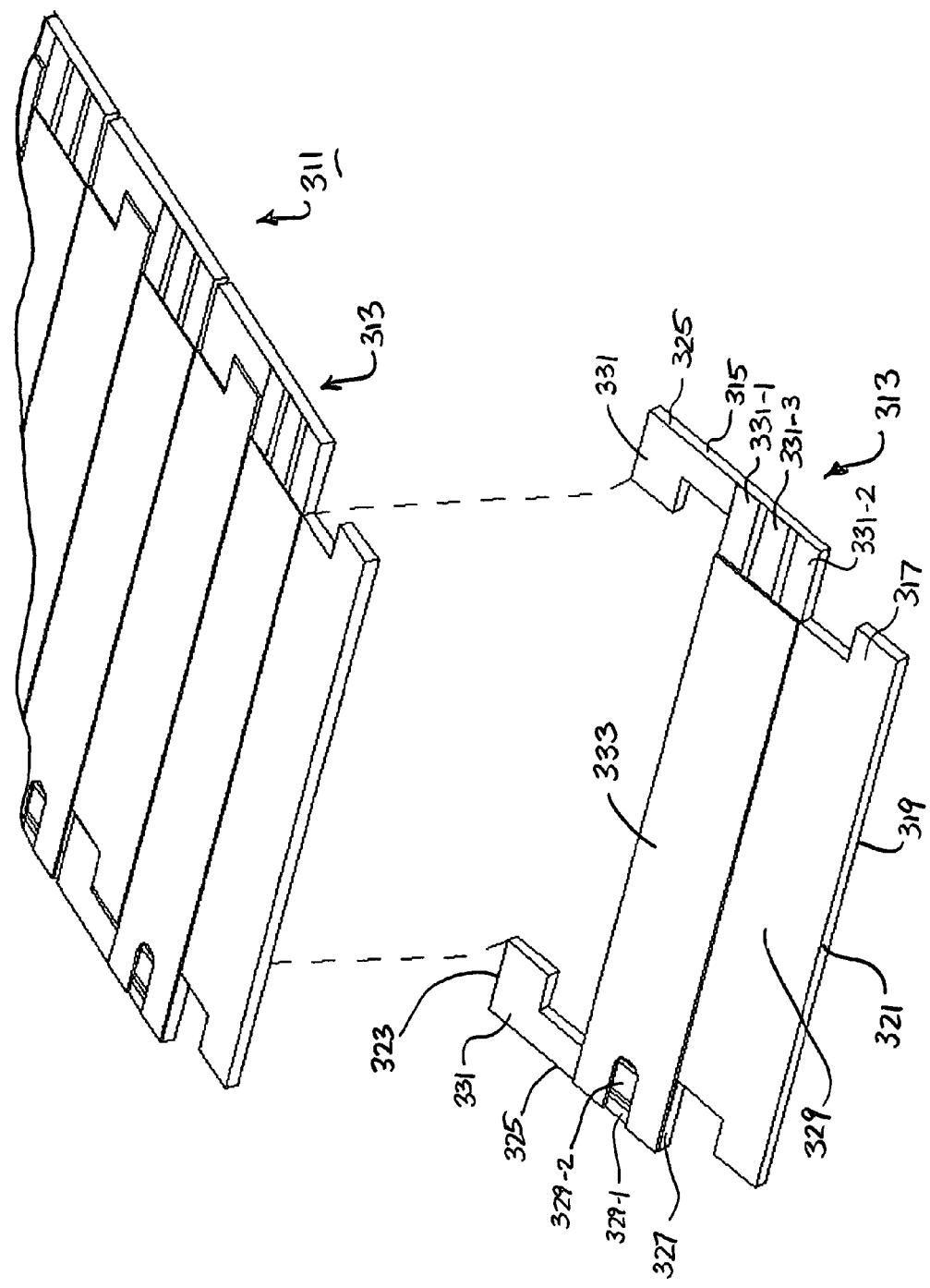
FIG. 15 is a fragmentary, top, front, right side perspective view of the sensor array shown in FIG. 14, the sensor array being shown with a single test sensor exploded therefrom.

Referring now to FIGS. 14 and 15, there is shown a fourth embodiment of a sensor array which is constructed according to the teachings of the present invention, the sensor array being identified generally by reference numeral 311. Sensor array 311 is similar to sensor array 11 in that sensor array 311 includes a plurality of test sensors 313 which are arranged in a front-to-back arrangement. However, sensor array 311 differs from sensor array 11 in the manner in which test sensors 313 are interconnected. Specifically, sensor array 311 includes a plurality of separate test sensors 313 which are adapted to interlock with one another to form a continuous chain, as will be described in further detail below.

As seen most clearly in FIG. 15, each test sensor 313 includes a unitary, non-conductive substrate 315 which includes a substantially flat top surface 317, a substantially flat bottom surface 319, a front edge 321, a rear edge 323 and a pair of side edges 325. Substrate 315 is additionally shaped to include a substantially rectangular center portion 327, a T-shaped front end 329 which projects forward from rectangular portion 327, and a pair of opposing L-shaped fingers 331 which project rearward from rectangular portion 327.

Figure 17:
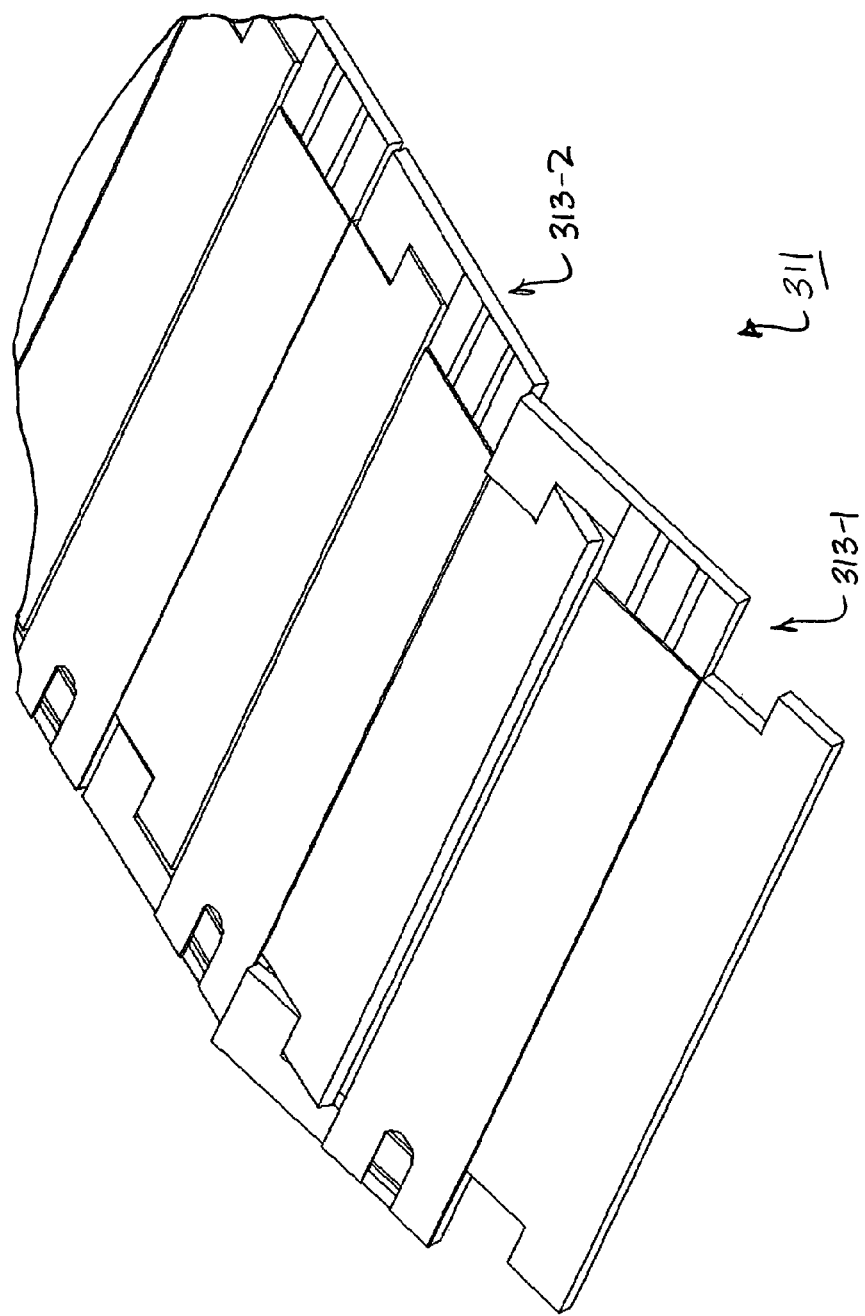
FIG. 17 is a fragmentary, top, front, right side perspective view of the sensor array shown in FIG. 14, the sensor array being shown with adjacent interlocking test sensors pivoted relative to one another so that the sensor array can more adequately conform to a non-planar surface.

It should be noted that the particular shape of each substrate 315 enables multiple test sensors 313 to be interlocked together to form a continuous array. Specifically, the pair of opposing L-shaped fingers 331 of the leading test sensor 313-1 are sized and shaped to interlock (i.e., engage) with the T-shaped front end 329 of the next successive test sensor 313-2, as seen most clearly in FIGS. 14 and 17. In this manner, a continuous chain of test sensors 313 can be interlocked together to form array 311.

It should be noted sensor array 311 is not limited to the aforementioned means for interlocking successive test sensors 313. Rather, it is to be understood that alternative means for interlocking separate test sensors 313 could be provided without departing from the spirit of the present invention. In particular, it is to be understood that the shape of substrate 315 for each test sensor 313 could be modified without departing from the spirit of the present invention.

Figure 16:
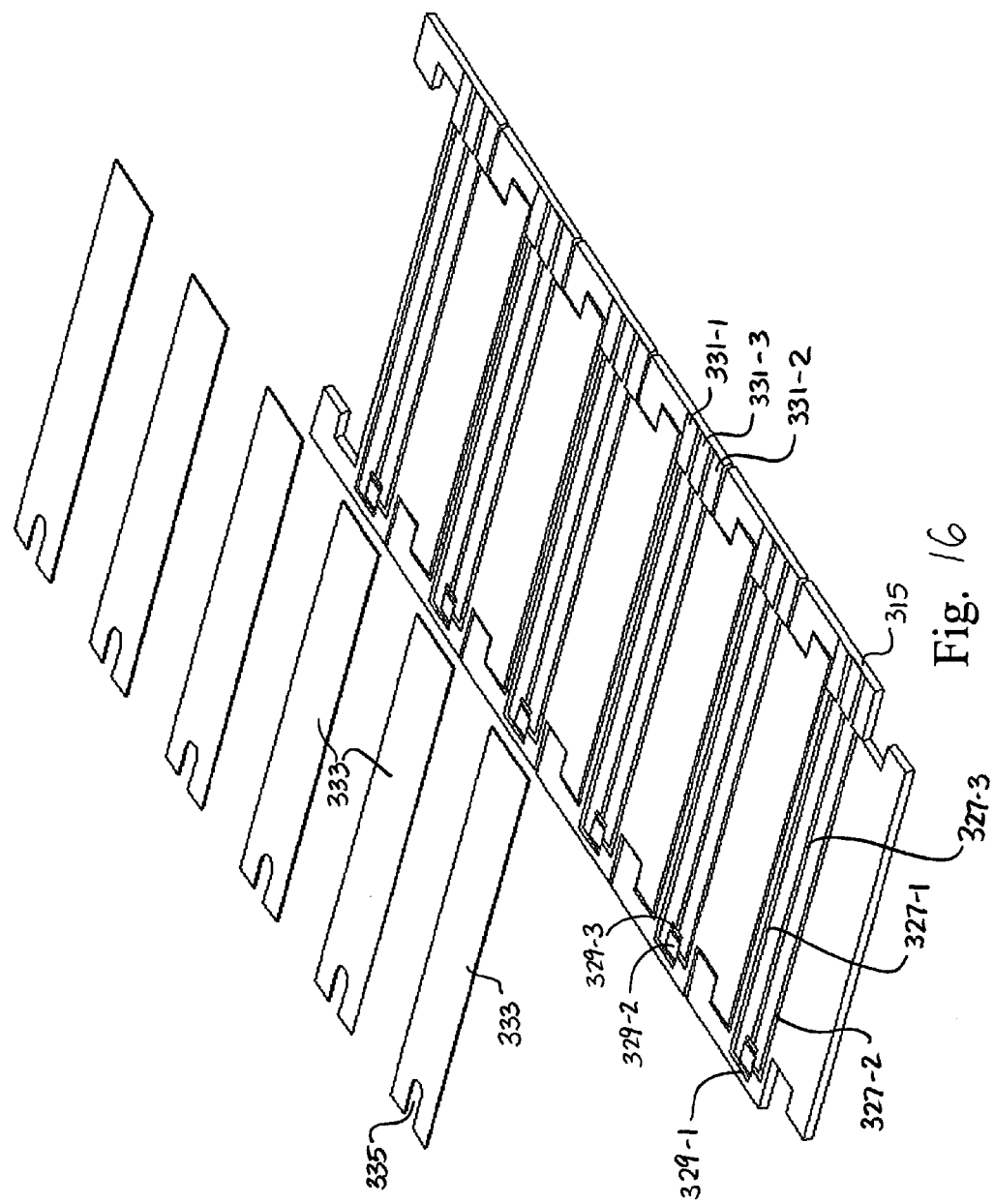
FIG. 16 is an exploded, top, front, right side perspective view of the sensor array shown in FIG. 14.

As seen most clearly in FIG. 16, a pair of carbon layer electrodes 327-1 and 327-2 are deposited onto top surface 317 of each substrate 315 in a spaced-apart relationship, electrode 327-1 serving as the reference electrode for test sensor 313 and electrode 327-2 serving as the working electrode for test sensor 313. An optional third electrode 327-3 may be provided which serves as the trigger electrode for test sensor 313.

Each electrode 327 is deposited onto substrate 313 in any conventional manner (e.g., screen printing) and includes a first end 329 and a second end 331. First end 329 of each electrode 327 is located along one side 325 of rectangular portion 327 and together define a reactive area for test strip 313. Second end 331 of each electrode 327 is located along the opposite side 325 of rectangular portion 327 and in position for connection with a compatible test meter. An enzyme (not shown) which produces an electrical reaction when exposed to a particular analyte (e.g., glucose) is applied to second end 331 of working electrode 327-2.

A mesh layer (not shown) is preferably disposed over first end 329 of electrodes 327. In this manner, the mesh layer would serve to adequately wick blood across the reaction area for the test sensor 313 so that a measurement can be undertaken.

A cover 333 constructed of a thin layer of insulate material is affixed to substrate 315 over electrodes 327 to preserve the integrity of each test sensor 313. Each cover 333 is shaped to define a narrow slot 335 along one end, slot 335 aligning directly above the mesh layer so as to provide a window through which a blood sample can be deposited onto test sensor 313.

As noted above, successive test sensors 313 interlock with one another to form sensor array 311. As seen most clearly in FIG. 17, the particular interlocking arrangement between separate test sensors 313 enables sensor array 311 to pivot, or hinge, about the point of interconnection so as to enable sensor array 311 to more closely conform to a non-planar surface, which is a principal object of the present invention. Furthermore, because each test sensor 313 in sensor array 311 is separate from one another, used test sensors 313 can be easily removed from the remainder of sensor array 311, which is highly desirable.

The embodiments shown in the present invention are intended to be merely exemplary and those skilled in the art shall be able to make numerous variations and modifications to it without departing from the spirit of the present invention. For example, it is to be understood that the use of blood channels and mesh layers to draw blood into the reaction area of a test sensor could be interchanged without departing from the spirit of the present invention. All such variations and modifications are intended to be within the scope of the present invention as defined in the appended claims.

What is claimed is:

1. A blood glucose meter adapted to receive a disposable lancet and a plurality of sensors for effectively combining both lancing and measurement processes into a single device, comprising:
    a housing having an opening defined therein against which a user is to position a penetration location of the user's skin;
    a disposable lancet within the housing;
    a lancet holder for mounting the lancet and driving the lancet through the opening to penetrate the skin of the user at the penetration location;
    a plurality of sensors mounted within the housing and disposed along a feed track, each of the plurality of sensors including a substrate;
    mechanical linkages within the meter for automatically indexing the sensors along the feed track; and
    a power source and electrodes for providing electrical energy for performing an assay of body fluid drawn from the penetration location and applied to a sensor;
        wherein the plurality of sensors includes at least a first test sensor and a second test sensor separate from but interlocked with said first test sensor; and
        wherein said substrate of the first test sensor includes a pair of pins sized and shaped to interlock with a pair of recesses formed in the substrate of said second test sensor.

2. The blood glucose meter of claim 1, further comprising a display for showing test results.

3. The blood glucose meter of claim 1, wherein the second test sensor is hingedly coupled to said first test sensor.

4. The blood glucose meter of claim 1, wherein the plurality of test sensors comprises:
    a unitary member coupled to said first and second test sensors.

5. The blood glucose meter of claim 1, wherein each of said substrates comprises:
    a top surface and a bottom surface;
    a first set of electrodes deposited on the top surface of said substrate; and
    a cover affixed to said substrate over said first set of electrodes.

6. The blood glucose meter of claim 1, wherein each of said substrates comprises:
    a top surface and a bottom surface; and
    a plurality of electrodes deposited on the top surface of said substrate in a spaced apart configuration and defining a reactive area.

* * * * *